(12) United States Patent
Poolman et al.

(10) Patent No.: US 11,484,582 B2
(45) Date of Patent: *Nov. 1, 2022

(54) METHODS AND COMPOSITIONS FOR IMMUNE PROTECTION AGAINST EXTRA-INTESTINAL PATHOGENIC E. COLI

(71) Applicants: Glaxosmithkline Biologicals S.A., Rixensart (BE); Janssen Pharmaceuticals, Inc., Titusville, NJ (US)

(72) Inventors: Jan Theunis Poolman, Haalem (NL); Bert Jacquemyn, Mechelen (BE); Darren Robert Abbanat, Cornwall, NY (US); Patricia Ibarra Yon, Solothurn (CH); Peter Wilhelmus Maria Hermans, Huissen (NL); Michael Thomas Kowarik, Zurich (CH); Michael Lukas Wetter, Zurich (CH); Stefan Jochen Kemmler, Zurich (CH); Micha Andres Häuptle, Zurich (CH); Veronica Gambillara Fonck, Meilen (CH); Manuela Mally, Watt (CH)

(73) Assignees: Janssen Pharmaceuticals, Inc., Titusville, NJ (US); Glaxosmithkline Biologicals S.A.

( * ) Notice: Subject to any disclaimer, the term of this patent is extended or adjusted under 35 U.S.C. 154(b) by 4 days.

This patent is subject to a terminal disclaimer.

(21) Appl. No.: 16/781,526

(22) Filed: Feb. 4, 2020

(65) Prior Publication Data

US 2021/0046171 A1  Feb. 18, 2021

Related U.S. Application Data

(63) Continuation of application No. 15/754,867, filed as application No. PCT/US2016/048278 on Aug. 24, 2016, now Pat. No. 10,583,185.

(60) Provisional application No. 62/209,091, filed on Aug. 24, 2015, provisional application No. 62/210,655, filed on Aug. 27, 2015.

(51) Int. Cl.

| | |
|---|---|
| *A61K 39/02* | (2006.01) |
| *A61K 47/64* | (2017.01) |
| *C08B 37/00* | (2006.01) |
| *A61P 31/04* | (2006.01) |
| *A61K 39/385* | (2006.01) |
| *A61K 39/108* | (2006.01) |
| *A61K 39/00* | (2006.01) |

(52) U.S. Cl.
CPC ........ *A61K 39/0258* (2013.01); *A61K 39/385* (2013.01); *A61K 47/646* (2017.08); *A61K 47/6415* (2017.08); *A61P 31/04* (2018.01); *C08B 37/0063* (2013.01); *A61K 2039/545* (2013.01); *A61K 2039/55583* (2013.01); *A61K 2039/6037* (2013.01); *A61K 2039/6087* (2013.01); *A61K 2039/70* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 3,700,612 | A | 10/1972 | Fath |
| 5,057,540 | A | 10/1991 | Kensil |
| 5,370,872 | A | 12/1994 | Cryz |
| 9,700,612 | B2 | 7/2017 | Kowarik |
| 10,159,751 | B2 | 12/2018 | Labovitiadi |
| 2014/0038296 | A1 | 2/2014 | Palsson |
| 2015/0238588 | A1 | 8/2015 | Kowarik |

FOREIGN PATENT DOCUMENTS

| | | |
|---|---|---|
| CN | 101983070 | 3/2011 |
| GB | 2220211 A | 1/1990 |
| JP | 2011514155 | 5/2011 |
| JP | 2017507178 | 3/2017 |
| WO | 2003074687 A1 | 9/2003 |
| WO | 2006119987 A2 | 11/2006 |
| WO | 2007109812 A2 | 9/2007 |
| WO | 2007109813 A1 | 9/2007 |
| WO | 2009089396 A2 | 7/2009 |
| WO | 2009104074 A2 | 8/2009 |
| WO | 2011062615 | 5/2011 |
| WO | 2012078482 A1 | 6/2012 |
| WO | 2013034664 A1 | 3/2013 |
| WO | 2014037585 A1 | 3/2014 |
| WO | 2014057109 A1 | 4/2014 |

(Continued)

OTHER PUBLICATIONS

International Search Report and Written Opinion for App. No. PCT/US2020/023415, dated Jun. 12, 2020, 21 pages.

(Continued)

*Primary Examiner* — Oluwatosin A Ogunbiyi
(74) *Attorney, Agent, or Firm* — Ice Miller LLP

(57) ABSTRACT

Compositions and methods are described for inducing an immune response against extra-intestinal pathogenic *Escherichia coli* (ExPEC) to thereby provide immune protection against diseases associated with ExPEC. In particular, compositions and methods are described for using conjugates of *E. coli* polysaccharide antigens O25B, O1A, O2, and O6A covalently bound to a detoxified exotoxin A of *Pseudomonas aeruginosa* (EPA) carrier protein as vaccines for the prevention of invasive ExPEC disease caused by ExPEC serotypes O1A, O2, O6A and O25B.

20 Claims, 7 Drawing Sheets

Specification includes a Sequence Listing.

(56) References Cited

FOREIGN PATENT DOCUMENTS

| | | | |
|---|---|---|---|
| WO | 2014102265 A1 | 7/2014 | |
| WO | 2014111516 A1 | 7/2014 | |
| WO | 2015052344 | 4/2015 | |
| WO | 2015117711 A1 | 8/2015 | |
| WO | 2015124769 A1 | 8/2015 | |
| WO | 2016107818 A1 | 7/2016 | |
| WO | 2016107819 A1 | 7/2016 | |
| WO | 2017035181 A1 | 3/2017 | |

OTHER PUBLICATIONS

Van Den Dobbelsteen et al.,"Immunogenicity and safety of tetravalent *Escherichia coli* O-antigen bioconjugate vaccine in animal models," Vaccine, vol. 34, No. 35, pp. 4152-4160 (2016).
Cryz Jr. et al., "Synthesis and Characterization of *Escherichia coli* O18 O-Polysaccharide Conjugate Vaccines," Infection and Immunity, vol. 58, No. 2, pp. 373-377 (1990).
Ihssen et al., "Production of glycoprotein vaccines in *Escherichia coli*," Microbial Cell Factories, vol. 9, No. 61, pp. 1-13 (2010).
Poolman et al., "Extraintestinal Pathogenic *Escherichia coli*, a Common Human Pathogen: Challenges for Vaccine Development and Progress in the Field," Journal of Infectious Diseases, vol. 213, pp. 6-13 (2016).
Jiang et al., "Tungsten-Induced Protein Aggregation: Solution Behavior," Wiley InterScience, vol. 98, No. 12, pp. 4695-4710 (2009).
Seidl et al., "Tungsten-Induced Denaturation and Aggregation of Epoetin Alfa During Primary Packaging as a Cause of Immunogenicity," Pharm. Res., vol. 29, pp. 1454-1467 (2012).
"Typhoid Vi Polysaccharide Vaccine Typhim VI," Sanofi Pasteur Inc., vol. 3., pp. 1-26 (Mar. 2014).
Stenutz R et al, "The structures of *Escherichia coli* O-polysaccharide antigens.", FEMS Microbiol Rev. May 2006;30(3):382-403.
V. Szijarto et al., "Diagnostic Potential of Monoclonal Antibodies Specific to the Unique O-Antigen of Multidrug-Resistant Epidemic *Escherichia coli* Clone ST131-O25b:H4", Clinical and Vaccine Immunology, (Apr. 30, 2014), vol. 21, No. 7, doi:10.1128/CVI.00685-13, ISSN 1556-6811, pp. 930-939, XP055179667.
Rogers B.A. et al., "*Escherichia coli* O25b-ST131: a pandemic, multiresistant, community-associated strain", Journal of Antimicrobial Chemotherapy, 2011, vol. 66, No. 1, pp. 1-14.
Pitout et al., "Extraintestinal Pathogenic *Escherichia coli*: An Update on Antimicrobial Resistance, Laboratory Diagnosis and Treatment," Expert Rev. Anti. Infect. Then, vol. 10, No. 10, pp. 1165-1176 (2012).
Mario F Feldman et al, "Engineering N-linked protein glycosylation with diverse O antigen lipopolysaccharide structures in *Escherichia coli*", Proceedings of the National Academy of Sciences, vol. 102, No. 8, pp. 3016-3021, (Feb. 9, 2005).
Fratamico et al., "*Escherichia coli* serogroup O2 and O28ac O-antigen gene cluster sequences and detection of pathogenic *Escherichia coil* O2 and O28ac by PCR," Canadian Journal of Microbiology, vol. 56, No. 4, pp. 308-316 (2010).
Jann et al., "Structural Comparison of the O6 Specific Polysaccharides From *Escherichia coli* O6:K2:H1, *Escherichia coli* O6:K13:H1, and *Escherichia coli* O6:K54:H10," Carbohydrate Research, vol. 263, No. 2, pp. 217-225 (1994).
Jansson et al., "Structural studies of the *Escherichia coli* O-antigen 6," Carbohydrate Research, vol. 131, No. 2, pp. 277-283 (1984).
Wacker et al., "N-linked glycosylation in Campylobacter jejuni and its functional transfer into *Escherichia coli*," Science, vol. 298, No. 5599, pp. 1790-1793 (2002).
Debroy et al., "Detection of O antigens in *Escherichia coli*," Animal Health Research Reviews, vol. 12, No. 2, pp. 169-185 (2011).
Datsenko et al., "One-step inactivation of chromosomal genes in *Escherichia coli* K-12 using PCR products," PNAS, vol. 97, No. 12, pp. 6640-6645 (2000).

Blanco et al., "Virulence factors and 0 groups of *Escherichia coli* isolates from patients with acute pyelonephritis, cystitis and asymptomatic bacteriuria," Eur. J. Epidemiol., vol. 12, No. 2, pp. 191-198 (1996).
Molina-Lopez et al., "Drug resistance, serotypes, and phylogenetic groups among uropathogenic *Escherichia coli* including O25-ST131 in Mexico City," J Infect Dev Ctries, vol. 5, No. 12, pp. 840-849 (2011).
Terai et al., "*Escherichia coli* Virulence Factors and Serotypes in Acute Bacterial Prostatitis," Int. Journal of Urology, vol. 4, No. 3, pp. 289-294 (1997).
Kenne et al., "Structural studies of the *Escherichia coli* O-antigen 25," Carbohydrate Research, vol. 122, No. 2, pp. 249-256 (1983).
Fundin et al., "NMR analysis of the O-antigen polysaccharide from *Escherichia coli* strain F171," Magnetic Resonance in Chemistry, vol. 41, No. 3, pp. 202-205 (2003).
Johnson et al., "*Escherichia coli* sequence type ST131 as an emerging fluoroquinolone-resistant uropathogen among renal transplant recipients," Antimicrob Agents Chemother. vol. 54, No. 1, pp. 546-550 (2010).
Banerjee et al., "A new clone sweeps clean: the enigmatic emergence of *Escherichia coli* sequence type 131," Antimicrob Agents Chemother. vol. 58, No. 9, pp. 4997-5004 (2014).
Lukac et al., "Toxoid of Pseudomonas aeruginosa exotoxin A generated by deletion of an active-site residue," Infect Immun, vol. 56, No. 12, pp. 3095-3098 (1988).
Szijarto et al. "The rapidly emerging ESBL-producing *Escherichia coil* O25-ST131 clone carries LPS core synthesis genes of the K-12 type," FEMS Microbiol. Lett., vol. 332, pp. 131-136 (2012).
Clermont et al,"The CTX-M-15-producing *Escherichia coli* diffusing clone belongs to a highly virulent B2 phylogenetic subgroup," J. Antimicrob. Chemother., vol. 61, No. 5, pp. 1024-1028 (2008).
Blanco et al.,"Molecular epidemiology of *Escherichia coli* producing extended-spectrum {beta}-lactamases in Lugo (Spain): dissemination of clone O25b:H4-ST131 producing CTX-M-15," J. Antimicrob. Chemother., vol. 63, pp. 1135-1141 (2009).
Phan et al., "The serum resistome of a globally disseminated multidrug resistant uropathogenic *Escherichia coil* clone," PLOS Genetics, vol. 9, No. 10, pp. 1-18 (2013).
Stevenson et al., "Structure of the O antigen of *Escherichia coli* K-12 and the sequence of its rfb gene cluster," J. Bacteriol., vol. 176, No. 13, pp. 4144-4156 (1994).
Amor et al., "Distribution of core oligosaccharide types in lipopolysaccharides from *Escherichia coli*," Infect. Immun., vol. 68, No. 3, pp. 1116-1124 (2000).
Jansson et al., "Structural studies of the O-specific side-chains of the *Escherichia coli* O2 lipopolysaccharide," Carbohydrate Res., vol. 161, pp. 273-279 (1987).
A. Cross et al, "Safety and Immunogenicity of a Polyvalent *Escherichia coli* Vaccine in Human Volunteers", Journal of Infectious Diseases. JID, Chicago, IL., (Oct. 1, 1994), vol. 170, No. 4, doi:10.1093/infdis/170.4.834, ISSN 0022-1899, pp. 834-840, XP055311603.
Cryz S J et al, "Synthesis and characterization of a polyvalent *Escherichia coli* O-polysaccharide-toxin A conjugate vaccine", Vaccine, Elsevier Ltd, GB, (Jan. 1, 1995), vol. 13, No. 5, doi:10.1016/0264-410X(94)00009-C, ISSN 0264-410X, pp. 449-453, XP004057719.
Int'l Search Report and Written Opinion dated Jun. 15, 2015 in Int'l Application No. PCT/EP2015/053739.
Int'l Search Report and Written Opinion dated Oct. 27, 2016 in Int'l Application No. PCT/US2016/048278.
Jadhav et al., "Virulence characteristics and genetic affinities of multiple drug resistant uropathogenic *Escherichia coli* from a Semi Urban Locality in India," PLOS One, vol. 6, No. 3, (2011).
Mora et al, "Emergence of clonal groups O1:HNM-D-ST59, O15:H1-D-ST393, O20:H34/HNM-D-ST354, O25b:H4-B2-ST131 and ONT:H21,42-B1-ST101 among CTX-M-14-producing *Escherichia coli* clinical isolates in Galicia, northwest Spain," International J. of Antimicrob. Agents, vol. 37, No. 1, pp. 16-21 (2011).
Clermont et al., "Rapid Detection of the O25b-ST131 clone of *Escherichia coil* encompassing the CTX-M-15- producing strains," Journal of Antimicrobial Chemotherapy, vol. 64, No. 2, pp. 274-277 (2009).

(56) References Cited

OTHER PUBLICATIONS

Glover et al., "Chemoenzymatic synthesis of Glycopeptides with PgIB, a bacterial oligosaccharyl transferase from Campylobacter jejuni," Chemistry and Biology, Current Biology, vol. 12, No. 12, pp. 1311-1316 (2005).

Laurentin et al., "A Microtiter Modification of the anthrone-sulfuric acid colorimetric assay for glucose-based carbohydrates", Analytical Biochemistry, 315, pp. 143-145, 2003.

Russo et al., "A killed, genetically engineered derivative of a wild-type extraintestinal pathogenic *E coli* strain is a caccine candidate", Elsevier, Vaccine 25, pp. 3859-3870, 2007.

Russo et al., "Medical and Exonomic impact of extraintestinal infections due to *Escherichia coli*: focus on an Increasingly important endemic problem", Elsevier, Microbes and Infection 5, pp. 449-456, 2003.

Kohler et al., "What defines extraintestinal pathogenic *Escherichia coli*", Elsevier, International journal of Medical Microbiology 301, pp. 642-647, 2011.

Ho et al., Preclinical Laboratory Evaluation of a Bivalent *Staphylococcus aureus* Saccharide-Exotoxin a Protein Conjugate Vaccine, Human vaccines, 2:3, pp. 89-98, May/Jun. 2006.

Lipsitch, "Bacterial vaccines and Serotype Replacement: Lessons from Haemophilus Influenzae and Prospects for *Streptococcus pneumoniae*", Emerging Infectious Diseases, vol. 5, No. 3, May/Jun. 1999.

Schito et al., "The ARESC study: an international survey on the antimicrobial resistance of pathogens involved in uncomplicated urinary tract infections", Elsevier, International Journal of Antimicrobial Agents 34, pp. 407-413, 2009.

Foxman, "Epidemiology of Urinary Tract Infections: Incidence, morbidity, and Economic Costs", The American Journal of Medicine, vol. 113(1A), 5S-13S, Jul. 2002.

Johnson et al., Extraintestinal Pathogenic *Escherichi coli*: "The other bad *E coli*", J Lab Clin Med., 139(3), pp. 155-162, 2002.

Kim et al., "Efficiency of a pneumococal Opsonophagocytic Killing Assay Improved by Multiplexing and by Colloring Colonies", Clinical and Dianostic laboratory Immunology, pp. 616-621, Jul. 2003.

Int'l Search Report and Written Opinion dated Jul. 20, 2017 in Int'l Application No. PCT/US2016/048278.

Int'l Preminary Report on Patentability dated Feb. 14, 2019 in Int'l Application No. PCT/EP2017/077123.

Written Opinion dated Dec. 21, 2018 in Int'l Application No. PCT/EP2017/077123.

Written Opinion of the International Preliminary Examining Authority dated Sep. 11, 2018 in PCT/EP2017/077123.

Written opinion of the Int'l Searching Authority dated Jan. 24, 2018 in Int'l Application No. PCT/EP2017/077123.

Int'l Search Report issued Jan. 24, 2018 in Int'l Application No. PCT/EP2017/077123.

Stoute et al., "A Preliminary Evaluation of a Recombinant Circumsporozoite Protein Vaccine Against Plasmodium Falciparum Malaria," New England Journal of Medicine, vol. 336, pp. 86-91 (1997).

Extended Search Report dated Apr. 12, 2017 in EP Application No. 16195256.9.

Frenck, et al., "Safety and Immunogenicity of a vaccine for extraintestinal pathogenic *Escherichia coli* (ESTELLA): a phase 2 randomised controlled trial," Lancet Infect. Dis. vol. 1, No. 6, pp. 631-640 (2019).

Paired t test; ns: not significant; ** P < 0.0001; Box plot median, 5% and 95% percentile Paired t test of log-transformed values: ns, not significant; **P<0.0001;
Box plot median, 5% and 95% percentile Paired t test of log-transformed values: ns, not significant; ****P<0.0001;
Box plot median, 5% and 95% percentile Paired t test of log-transformed values: ns, not significant; ****P<0.0001;
Box plot median, 5% and 95% percentile Paired t test of log-transformed values: ns, not significant; ****P<0.0001;
Box plot median, 5% and 95% percentile

SEQUENCE LISTING

<160> NUMBER OF SEQ ID NOS: 3

<210> SEQ ID NO 1
<211> LENGTH: 652
<212> TYPE: PRT
<213> ORGANISM: Artificial Sequence
<220> FEATURE:
<223> OTHER INFORMATION: Detoxified EPA protein comprising 4 optimized
      N-glycosylation sequences

<400> SEQUENCE: 1

Gly Ser Gly Gly Gly Asp Gln Asn Ala Thr Gly Ser Gly Gly Gly Lys
1               5                   10                  15

Leu Ala Glu Glu Ala Phe Asp Leu Trp Asn Glu Cys Ala Lys Ala Cys
            20                  25                  30

Val Leu Asp Leu Lys Asp Gly Val Arg Ser Ser Arg Met Ser Val Asp
        35                  40                  45

Pro Ala Ile Ala Asp Thr Asn Gly Gln Gly Val Leu His Tyr Ser Met
    50                  55                  60

Val Leu Glu Gly Gly Asn Asp Ala Leu Lys Leu Ala Ile Asp Asn Ala
65                  70                  75                  80

Leu Ser Ile Thr Ser Asp Gly Leu Thr Ile Arg Leu Glu Gly Gly Val
                85                  90                  95

Glu Pro Asn Lys Pro Val Arg Tyr Ser Tyr Thr Arg Gln Ala Arg Gly
            100                 105                 110

Ser Trp Ser Leu Asn Trp Leu Val Pro Ile Gly His Glu Lys Pro Ser
        115                 120                 125

Asn Ile Lys Val Phe Ile His Glu Leu Asn Ala Gly Asn Gln Leu Ser
    130                 135                 140

His Met Ser Pro Ile Tyr Thr Ile Glu Met Gly Asp Glu Leu Leu Ala
145                 150                 155                 160

Lys Leu Ala Arg Asp Ala Thr Phe Phe Val Arg Ala His Glu Ser Asn
                165                 170                 175

Glu Met Gln Pro Thr Leu Ala Ile Ser His Ala Gly Val Ser Val Val
            180                 185                 190

Met Ala Gln Ala Gln Pro Arg Arg Glu Lys Arg Trp Ser Glu Trp Ala
        195                 200                 205

Ser Gly Lys Val Leu Cys Leu Leu Asp Pro Leu Asp Gly Val Tyr Asn
    210                 215                 220

Tyr Leu Ala Gln Gln Arg Cys Asn Leu Asp Asp Thr Trp Glu Gly Lys
225                 230                 235                 240

Ile Tyr Arg Val Leu Ala Gly Asn Pro Ala Lys His Asp Leu Asp Ile
                245                 250                 255

Lys Asp Asn Asn Asn Ser Thr Pro Thr Val Ile Ser His Arg Leu His
            260                 265                 270

Phe Pro Glu Gly Gly Ser Leu Ala Ala Leu Thr Ala His Gln Ala Cys
        275                 280                 285

His Leu Pro Leu Glu Ala Phe Thr Arg His Arg Gln Pro Arg Gly Trp
    290                 295                 300

Glu Gln Leu Glu Gln Cys Gly Tyr Pro Val Gln Arg Leu Val Ala Leu
305                 310                 315                 320

Tyr Leu Ala Ala Arg Leu Ser Trp Asn Gln Val Asp Gln Val Ile Arg
                325                 330                 335

```
Asn Ala Leu Ala Ser Pro Gly Ser Gly Asp Leu Gly Glu Ala Ile
                340                 345                 350

Arg Glu Gln Pro Glu Gln Ala Arg Leu Ala Leu Thr Leu Ala Ala Ala
            355                 360                 365

Glu Ser Glu Arg Phe Val Arg Gln Gly Thr Asn Asp Glu Ala Gly
    370                 375                 380

Ala Ala Ser Ala Asp Val Val Ser Leu Thr Cys Pro Val Ala Lys Asp
385                 390                 395                 400

Gln Asn Arg Thr Lys Gly Glu Cys Ala Gly Pro Ala Asp Ser Gly Asp
                405                 410                 415

Ala Leu Leu Glu Arg Asn Tyr Pro Thr Gly Ala Glu Phe Leu Gly Asp
            420                 425                 430

Gly Gly Asp Val Ser Phe Ser Thr Arg Gly Thr Gln Asn Trp Thr Val
        435                 440                 445

Glu Arg Leu Leu Gln Ala His Arg Gln Leu Glu Arg Gly Tyr Val
    450                 455                 460

Phe Val Gly Tyr His Gly Thr Phe Leu Glu Ala Ala Gln Ser Ile Val
465                 470                 475                 480

Phe Gly Gly Val Arg Ala Arg Ser Gln Asp Leu Asp Ala Ile Trp Arg
                485                 490                 495

Gly Phe Tyr Ile Ala Gly Asp Pro Ala Leu Ala Tyr Gly Tyr Ala Gln
            500                 505                 510

Asp Gln Glu Pro Asp Ala Arg Gly Arg Ile Arg Asn Gly Ala Leu Leu
        515                 520                 525

Arg Val Tyr Val Pro Arg Trp Ser Leu Pro Gly Phe Tyr Arg Thr Gly
    530                 535                 540

Leu Thr Leu Ala Ala Pro Glu Ala Ala Gly Glu Val Glu Arg Leu Ile
545                 550                 555                 560

Gly His Pro Leu Pro Leu Arg Leu Asp Ala Ile Thr Gly Pro Glu Glu
                565                 570                 575

Glu Gly Gly Arg Val Thr Ile Leu Gly Trp Pro Leu Ala Glu Arg Thr
            580                 585                 590

Val Val Ile Pro Ser Ala Ile Pro Thr Asp Pro Arg Asn Val Gly Gly
        595                 600                 605

Asp Leu Asp Pro Ser Ser Ile Pro Asp Lys Glu Gln Ala Ile Ser Ala
    610                 615                 620

Leu Pro Asp Tyr Ala Ser Gln Pro Gly Lys Pro Pro Arg Glu Asp Leu
625                 630                 635                 640

Lys Leu Gly Ser Gly Gly Gly Asp Gln Asn Ala Thr
                645                 650

<210> SEQ ID NO 2
<211> LENGTH: 3
<212> TYPE: PRT
<213> ORGANISM: Artificial Sequence
<220> FEATURE:
<223> OTHER INFORMATION: N-glycosylation consensus sequence
<220> FEATURE:
<221> NAME/KEY: any amino acid (except Pro)
<222> LOCATION: (2)..(2)
<220> FEATURE:
<221> NAME/KEY: Ser or Thr
<222> LOCATION: (3)..(3)

<400> SEQUENCE: 2

Asn Xaa Xaa
1
```

```
<210> SEQ ID NO 3
<211> LENGTH: 5
<212> TYPE: PRT
<213> ORGANISM: Artificial Sequence
<220> FEATURE:
<223> OTHER INFORMATION: N-glycosylation consensus sequence
<220> FEATURE:
<221> NAME/KEY: Asp or Glu
<222> LOCATION: (1)..(1)
<220> FEATURE:
<221> NAME/KEY: any natural amino acid except Pro
<222> LOCATION: (2)..(2)
<220> FEATURE:
<221> NAME/KEY: any natural amino acid except Pro
<222> LOCATION: (4)..(4)
<220> FEATURE:
<221> NAME/KEY: Ser or Thr
<222> LOCATION: (5)..(5)

<400> SEQUENCE: 3

Xaa Xaa Asn Xaa Xaa
1               5
```

METHODS AND COMPOSITIONS FOR IMMUNE PROTECTION AGAINST EXTRA-INTESTINAL PATHOGENIC E. COLI

CROSS REFERENCE TO RELATED APPLICATIONS

This application is a continuation of U.S. patent application Ser. No. 15/754,867, filed Feb. 23, 2018, now U.S. Pat. No. 10,583,185, which is a Section 371 of International Application No. PCT/US2016/048278, filed Aug. 24, 2016, which was published in the English language on Mar. 2, 2017, under International Publication No. WO 2017/035181, which claims priority under 35 U.S.C. § 119(e) to U.S. Provisional Patent Application No. 62/209,091 filed on Aug. 24, 2015, and to U.S. Provisional Patent Application No. 62/210,655, filed on Aug. 27, 2015, the disclosures of all of which are herein incorporated by reference in their entireties.

REFERENCE TO SEQUENCE LISTING SUBMITTED ELECTRONICALLY

This application contains a sequence listing, which is submitted electronically via EFS-Web as an ASCII formatted sequence listing with a file name "688097-86_Sequence Listing" and a creation date of Aug. 15, 2016 and having a size of 6.8 KB. The sequence listing submitted via EFS-Web is part of the specification and is herein incorporated by reference in its entirety.

FIELD OF THE INVENTION

This invention relates to compositions and methods for inducing an immune response against extra-intestinal pathogenic *Escherichia coli* (ExPEC) to thereby provide immune protection against diseases associated with ExPEC. In particular, embodiments of this invention relate to multivalent vaccines containing conjugates of *E. coli* polysaccharide antigens O25B, O1A, O2, and O6A each covalently bound to a detoxified exotoxin A of *Pseudomonas aeruginosa* carrier protein and uses of the vaccines to provide effective immune protection against ExPEC infection.

BACKGROUND OF THE INVENTION

Extra-intestinal pathogenic *E. coli* (ExPEC) are normally harmless inhabitants of human gut. However, ExPEC strains can possess virulence factors for the colonization and infection of sites outside of the gastrointestinal tract to cause diverse and serious invasive diseases, resulting in significant morbidity, mortality, and costs annually (see, e.g., Johnson et al., J Lab Clin Med. 2002; 139(3):155-162; Kohler et al., Int J Med Microbiol. 2011; 301(8):642-647; Foxman, Am J Med. 2002; 113 Suppl 1A:5S-13S; and Russo et al., Microbes Infect. 2003; 5(5):449-456). ExPEC strains are the most common cause of urinary tract infection (UTI). They are also a contributor to surgical site infections and neonatal meningitis (Johnson et al., 2002; and Russo et al., 2003), associated with abdominal and pelvic infections and nosocomial pneumonia, and are occasionally involved in other extra-intestinal infections such as osteomyelitis, cellulitis, and wound infections. All these primary sites of infection can result in ExPEC bacteremia (Russo et al., 2003).

Bacterial resistance to antibiotics is a major concern in the fight against bacterial infection, and multi-drug resistant (MDR) *E. coli* strains are becoming more and more prevalent (see, e.g., Schito et al., 2009, Int. J. Antimicrob. Agents 34(5):407-413; and Pitout et al., 2012, Expert Rev. Anti. Infect. Ther. 10(10):1165-1176). The emergence and rapid global dissemination of ExPEC sequence type 131 is considered the main driver of increased drug resistance, including multi-drug resistance (Johnson et al., Antimicrob Agents Chemother. 2010; 54(1):546-550; Rogers et al., J Antimicrob Chemother. 2011; 66(1):1-14). This clone is found in 12.5% to 30% of all ExPEC clinical isolates, mostly exhibits serotype O25B:H4, and shows high levels of fluoroquinolone resistance, which is often accompanied by trimethoprim/sulfamethoxazole resistance (Rogers et al, 2011, and Banerjee et al., Antimicrob Agents Chemother. 2014; 58(9): 4997-5004).

The O-antigen serotype is based on the chemical structure of the O polysaccharide antigen, the outer membrane portion of the lipopolysaccharide (LPS) in a Gram-negative bacterium. More than 180 *E. coli* O-antigens have been reported (Stenutz et al., FEMS Microbial Rev. 2006; 30: 382-403). ExPEC infection can be caused by any serotype. Although there is an overrepresentation of certain serotypes in ExPEC infection, surface polysaccharides from ExPEC isolates nonetheless exhibit considerable antigenic diversity, which makes the development of an ExPEC vaccine based on surface polysaccharides extremely challenging (Russo et al., Vaccine. 2007; 25: 3859-3870). Also, certain O-antigens may be poorly immunogenic. Furthermore, based on studies from Pneumococcal conjugate vaccines, when a number of serotypes can cause a disease, the vaccine composition, such as the choice of serotypes for inclusion in a vaccine and the dosage levels of the included serotypes, can be critical, since use of a vaccine against certain serotypes may potentially increase carriage of and disease from serotypes not included in the vaccine, or even a serotype that is included in the vaccine but only weakly effective in immunizing against the serotype (Lipsitch, Emerging Infectious Diseases; 1999, 5:336-345). Ideally, a vaccine should maximize its beneficial effects in the prevention of disease caused by serotypes included in the vaccine, while minimizing the risk of added disease from increased carriage of non-vaccine serotypes.

Accordingly, there is a need in the art for vaccines against ExPEC. In particular, there exists a need for an ExPEC vaccine based on surface polysaccharides that can be used to provide effective immune protection against ExPEC O25B serotype and other serotypes prevalent among ExPEC.

BRIEF SUMMARY OF THE INVENTION

It has been surprisingly discovered that an *E. coli* O25B antigen appears to be somewhat less immunogenic than other *E. coli* O-antigens (e.g., O1A, O2, and O6A) when tested as conjugates of the O-antigens each covalently bound to a detoxified exotoxin A of *P. aeruginosa* (EPA) carrier protein, and that vaccination with a composition containing EPA conjugates of *E. coli* O25B antigen and EPA conjugates of one or more additional *E. coli* O-antigens at an appropriate dose and ratio provides an improved immune response against the ExPEC O25B serotype and the one or more additional ExPEC O-serotypes.

Accordingly, in one general aspect, the invention relates to a composition comprising an *E. coli* O25B antigen at a first concentration of 8 to 48 µg/ml, and at least one additional *E. coli* O-antigen at a second concentration that is 10% to 100% of the first concentration, wherein each of the *E. coli* O25B antigen and the at least one additional *E. coli* O-antigen is independently covalently bound to an EPA carrier protein, and the composition is effective in inducing an immune response against the *E. coli* O25B antigen and the at least one additional *E. coli* O-antigen in a subject in need thereof. In a preferred embodiment, the at least one additional *E. coli* O-antigen is present at a second concentration of at least 5 µg/ml, more preferably, at a second concentration of least 8 µg/ml.

In one embodiment, the invention relates to a composition comprising an *E. coli* O25B antigen at a first concentration of 10 to 36 µg/ml, and at least one additional *E. coli* O-antigen selected from the group consisting of an *E. coli* O1A antigen, an *E. coli* O2 antigen and an *E. coli* O6A antigen, wherein each of the additional *E. coli* O-antigens has a concentration that is independently 50% to 100% of the first concentration of the *E. coli* O25B antigen in the composition, and each of the *E. coli* O25B, O1A, O2 and O6A antigens are independently covalently bound to an EPA carrier protein.

In one preferred embodiment, the invention relates to a composition comprising an *E. coli* O25B antigen at a first concentration of 10 to 36 µg/ml, and a second concentration of each of an *E. coli* O1A antigen, an *E. coli* O2 antigen and an *E. coli* O6A antigen, wherein each of the *E. coli* O25B, O1A, O2 and O6A antigens are independently covalently bound to an EPA carrier protein, and the ratio of the first concentration to the second concentration is 1:1 to 2:1. Preferably, the composition comprises the *E. coli* O25B, O1A, O2 and O6A antigen polysaccharides at a weight ratio of 1:1:1:1 or 2:1:1:1. More preferably, the composition comprises 16 or 32 µg/ml of the O25B antigen.

In another general aspect, the invention relates to a method of inducing an immune response to extra-intestinal pathogenic *E. coli* (ExPEC) in a subject in need thereof. The method comprises administering to the subject an *E. coli* O25B antigen at a first effective amount of 4 to 24 µg per administration, and at least one additional *E. coli* O-antigen at a second effective amount that is 10% to 100% of the first effective amount, wherein each of the *E. coli* O25B antigen and the at least one additional *E. coli* O-antigen is independently covalently bound to an EPA carrier protein, and the administration is effective in inducing an immune response against the *E. coli* O25B antigen and the at least one additional *E. coli* O-antigen in the subject. In a preferred embodiment, the at least one additional *E. coli* O-antigen is administered at a second effective amount of at least 3 µg per administration, more preferably, at a second effective amount of least 4 µg per administration. The *E. coli* O25B antigen and the at least one additional *E. coli* O-antigen can be administered in one composition or administered in combination from multiple compositions.

In one embodiment, the invention relates to a method of inducing an immune response to ExPEC in a subject in need thereof, comprising administering to the subject an *E. coli* O25B antigen at a first effective amount of 5 to 18 µg per administration, more preferably 8 to 16 µg per administration, and at least one additional *E. coli* O-antigen selected from the group consisting of an *E. coli* O1A antigen, an *E. coli* O2 antigen and an *E. coli* O6A antigen, wherein each of the additional *E. coli* O-antigens is administered at an effective amount that is independently 50% to 100% of the first effective amount of the *E. coli* O25B antigen, and each of the *E. coli* O25B, O1A, O2 and O6A antigens are independently covalently bound to an EPA carrier protein.

In one preferred embodiment, the invention relates to a method of inducing an immune response to ExPEC in a subject in need thereof, comprising administering to the subject an *E. coli* O25B antigen at a first effective amount of 5 to 18 µg per administration, more preferably 8 to 16 µg per administration, and a second effective amount of each of an *E. coli* O1A antigen, an *E. coli* O2 antigen and an *E. coli* O6A antigen, wherein each of the *E. coli* O25B, O1A, O2 and O6A antigens are independently covalently bound to an EPA carrier protein, and the ratio of the first effective amount to the second effective amount is 1:1 to 2:1. Preferably, the *E. coli* O25B, O1A, O2 and O6A antigens are administered at a dosage ratio of 1:1:1:1 or 2:1:1:1, and the *E. coli* O25B antigen is administered at 5 µg, 8 µg or 16 µg per administration. In a preferred embodiment, the *E. coli* O25B, O1A, O2 and O6A antigens are administered to the subject in one composition, more preferably, in compositions comprising the *E. coli* O25B, O1A, O2 and O6A antigens each independently covalently bound to an EPA carrier protein, wherein the concentrations of these O-antigens in the compositions are chosen from respectively 16:8:8:8 µg/ml (i.e., 16 µg/ml of O25B antigen, 8 µg/ml of O1A antigen, 8 µg/ml of O2 antigen, and 8 µg/ml of O6A antigen), 16:16:16:16 µg/ml, 32:16:16:16 µg/ml and 32:32:32:32 µg/ml. Preferably, 0.5 ml of such a composition is administered to a subject to achieve a dosage per administration of *E. coli* O25B, O1A, O2 and O6A antigens respectively at 8:4:4:4 µg (i.e., 8 µg of O25B antigen, 4 µg of O1A antigen, 4 µg of O2 antigen, and 4 µg of O6A antigen), 8:8:8:8 µg, 16:8:8:8 µg or 16:16:16:16 µg.

According to a preferred embodiment, the immune response induced by a method of the present invention prevents an invasive ExPEC disease caused by ExPEC serotypes O1A, O2, O6A and O25B in a human subject in need thereof. Diseases associated with ExPEC or ExPEC diseases include, but are not limited to, urinary tract infection, surgical-site infection, bacteremia, abdominal or pelvic infection, pneumonia, nosocomial pneumonia, osteomyelitis, cellulitis, pyelonephritis, wound infection, meningitis, neonatal meningitis, peritonitis, cholangitis, soft-tissue infections, pyomyositis, septic arthritis, and sepsis. Preferably, the human subject is an at-risk human subject, who has or is at risk of having an invasive ExPEC disease, such as an elderly human, a hospitalized patient, a human child, an immunocompromised human, a pregnant woman, people with diabetes or wound injuries, people who recently had or are scheduled to have a surgery, etc.

According to an embodiment of the invention, each of the O-antigen is covalently bound to the EPA carrier protein at the Asn residue of a glycosylation sequence comprising Asp (Glu)-X-Asn-Z-Ser (Thr) (SEQ ID NO: 3), wherein X and Z are independently selected from any natural amino acid except Pro. In a preferred embodiment, the EPA carrier protein comprises the amino acid sequence of SEQ ID NO: 1. In another embodiment, the O-antigen is covalently bound to the EPA carrier protein at a polysaccharide-to-protein weight ratio of 1:7 to 1:2, preferably, 1:5 to 1:2. For example, in an O-antigen/EPA conjugate according to an embodiment of the invention, the weight of the O-antigen can be 15% to 50%, or 20% to 40%, of the weight of the EPA.

Another aspect of the invention relates to a process of making a composition according to an embodiment of the invention, the process comprises combining the *E. coli* O25B, O1A, O2 and O6A antigens, each independently covalently bound to the EPA carrier protein, in one composition.

Yet another aspect of the invention relates to use of a composition according to an embodiment of the invention for the manufacture of a vaccine or medicament for inducing an immune response to ExPEC or for preventing or treating a disease associated with ExPEC in a subject in need thereof.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

In the drawings:

FIG. 3A: O2-EPA immunization; FIG. 3B: O6A-EPA immunization; and FIG. 3C: O25B-EPA immunization;

FIG. 5A: O1A-EPA; FIG. 5B: O2-EPA; FIG. 5C: O6A-EPA; and FIG. 5D: O25B-EPA; pre-injection (Day 1) and post-injection (30 days after injection), wherein a significant increase in the OI between post- and pre-injection (indicated by *, multiple * represents increased degree of significance) was observed only in the vaccinated groups; ns, no significant difference.

DETAILED DESCRIPTION OF THE INVENTION

Figure 1:
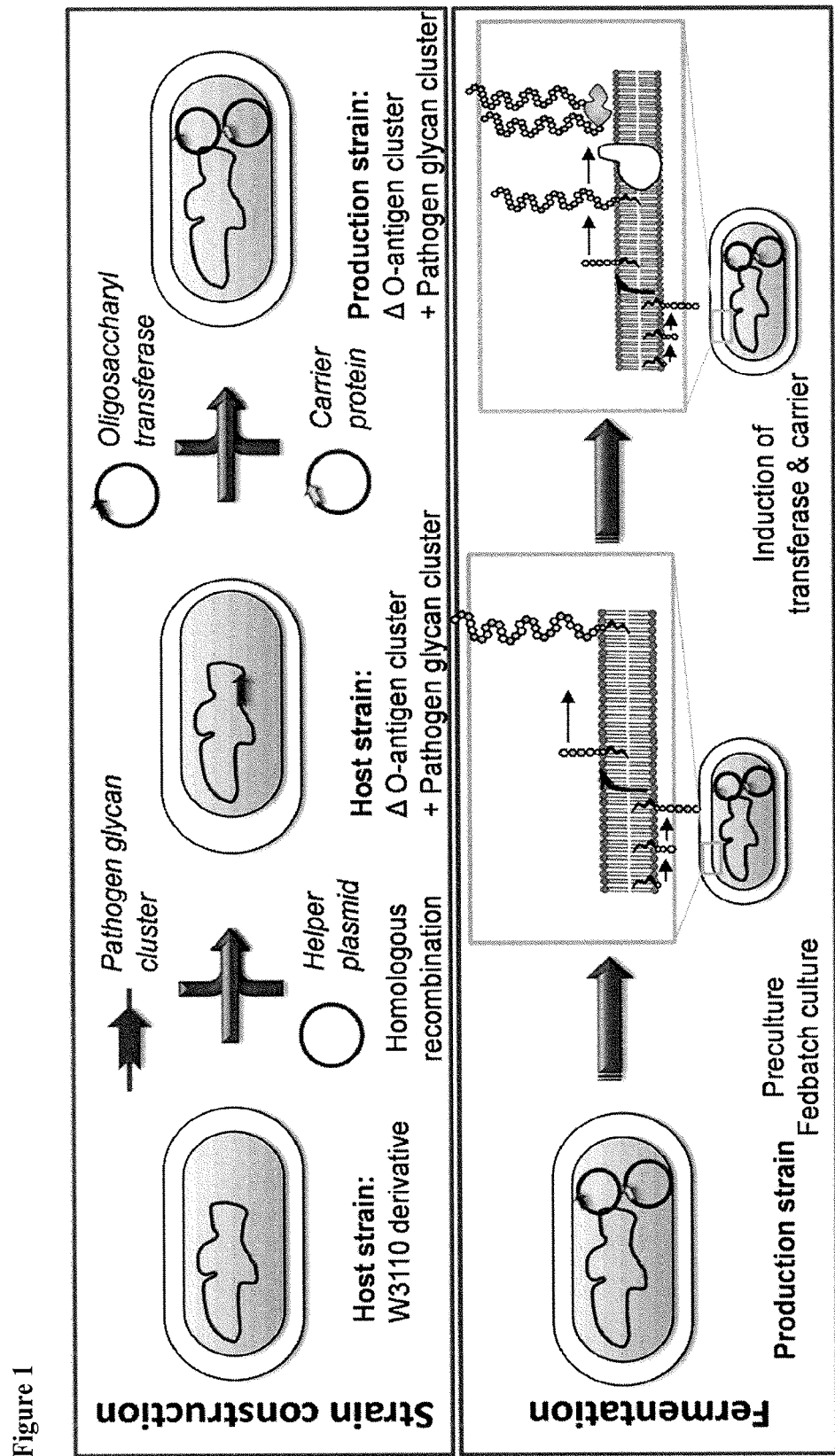
FIG. 1 is an exemplary representation of the glycoconjugate vaccine production platform: the cytoplasm (marked in grey) of the host cell contains all the DNA constructs necessary for the recombinant production of the O-antigen/EPA conjugate in the periplasm (marked in white) of the host cell.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning commonly understood to one of ordinary skill in the art to which this invention pertains. Otherwise, certain terms cited herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

As used herein, the terms "O polysaccharide," "O-antigen", "O antigen", "O-antigen polysaccharide," "O-polysaccharide antigen" and the abbreviation "OPS", all refer to the O antigen of Gram-negative bacteria, which is a component of the lipopolysaccharide (LPS) and is specific for each serotype or sero(sub)type of the Gram-negative bacteria. The O antigen usually contains repeating units (RUs) of two to seven sugar residues. As used herein, the RU is set equal to the biological repeat unit (BRU). The BRU describes the RU of an O-antigen as it is synthesized in vivo.

As used herein, the terms "conjugate" and "glycoconjugate" all refer to a conjugation product containing an E. coli O antigen covalently bound to a carrier protein. The conjugate can be a bioconjugate, which is a conjugation product prepared in a host cell, wherein the host cell machinery produces the O antigen and the carrier protein and links the O antigen to the carrier protein, e.g., via N-links. The conjugate can also be prepared by other means, for example, by chemical linkage of the protein and sugar antigen.

As used herein, the term "effective amount" in the context of administering an O antigen to a subject in methods according to embodiments of the invention refers to the amount of the O antigen that is sufficient to induce a desired immune effect or immune response in the subject. In certain embodiments, an "effective amount" refers to the amount of an O antigen which is sufficient to produce immunity in a subject to achieve one or more of the following effects in the subject: (i) prevent the development or onset of an ExPEC infection, preferably an invasive ExPEC disease, or symptom associated therewith; (ii) prevent the recurrence of an ExPEC infection, preferably an invasive ExPEC disease, or symptom associated therewith; (iii) prevent, reduce or ameliorate the severity of an ExPEC infection, preferably an invasive ExPEC disease, or symptom associated therewith; (iv) reduce the duration of an ExPEC infection, preferably an invasive ExPEC disease, or symptom associated therewith; (v) prevent the progression of an ExPEC infection, preferably an invasive ExPEC disease, or symptom associated therewith; (vi) cause regression of an ExPEC infection or symptom associated therewith; (vii) prevent or reduce organ failure associated with an ExPEC infection; (viii) reduce the chance or frequency of hospitalization of a subject having an ExPEC infection; (ix) reduce hospitalization length of a subject having an ExPEC infection; (x) increase the survival of a subject with an ExPEC infection, preferably an invasive ExPEC disease; (xi) eliminate an ExPEC infection, preferably an invasive ExPEC disease; (xii) inhibit or reduce ExPEC replication; and/or (xiii) enhance or improve the prophylactic or therapeutic effect(s) of another therapy.

An "effective amount" can vary depending upon a variety of factors, such as the physical condition of the subject, age, weight, health, etc.; route of administration, such as oral or parenteral; the composition administered, such as the target O antigen, the other co-administered O antigens, adjuvant, etc.; and the particular disease for which immunity is desired. When the O antigen is covalently bound to a protein carrier, the effective amount for the O antigen is calculated based on only the O antigen polysaccharide moiety in the conjugate.

As used herein, the term "in combination," in the context of the administration of two or more O antigens or compositions to a subject, does not restrict the order in which O antigens or compositions are administered to a subject. For example, a first composition can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second composition to a subject.

As used herein, "subject" means any animal, preferably a mammal, most preferably a human, to who will be or has been vaccinated by a method or composition according to an embodiment of the invention. The term "mammal" as used herein, encompasses any mammal. Examples of mammals include, but are not limited to, cows, horses, sheep, pigs, cats, dogs, mice, rats, rabbits, guinea pigs, monkeys, humans, etc., most preferably a human. In some embodiments, a subject is a human infant. In another embodiment, a subject is a human child. In another embodiment, a subject is a human adult. In a specific embodiment, a subject is an at-risk human adult. In another embodiment, a subject is an elderly human. In another embodiment, a subject is a human infant, including a premature human infant and a human infant born at term. In another embodiment, a subject is a human toddler. The terms "subject" and "patient" may be used herein interchangeably.

As used herein, the term "premature human infant" refers to a human infant born at less than 37 weeks of gestational age.

As used herein, the term "human infant" refers to a newborn to 1 year old human.

As used herein, the term "human toddler" refers to a human that is 1 year to 3 years old.

As used herein, the term "human child" refers to a human that is 1 year to 18 years old.

As used herein, the term "human adult" refers to a human that is 18 years or older.

As used herein, the term "at-risk human adult" refers to a human that is 18 years or older who is more prone to ExPEC infection than the average human adult population. Examples of "at-risk human adult" include, but not limited to, elderly humans, immunocompromised humans, pregnant women, people with diabetes or wound injuries, people who recently had or are scheduled to have a surgery, etc.

As used herein, the term "elderly human" refers to a human that is 55, preferably 60, more preferably 65, years or older.

As used herein, an "invasive ExPEC disease" is defined as isolation and identification of ExPEC from normally sterile body sites in a subject presenting with an acute illness consistent with bacterial infection.

As used herein, an "immunological response" or "immune response" to an antigen or composition refers to the development in a subject of a humoral and/or a cellular immune response to the antigen or an antigen present in the composition.

It has been surprisingly discovered in the invention that E. coli O25B antigen conjugated to an EPA carrier protein appears to be less immunogenic than the other E. coli O-antigens (e.g., O1A, O2, and O6A) conjugated to the EPA carrier protein. This discovery leads to further investigation into the dosage of E. coli O25B antigen and the dosage ratios of various E. coli O antigens within a multivalent vaccine, thus the development of multivalent vaccines and immunization methods based on E. coli O antigens for improved immune responses against the O25B serotype and other serotypes of ExPEC.

Epidemiology

Studies on the serotype distribution of E. coli causing ExPEC disease indicate that 10 predominant O serotypes could cover an estimated 60-80% of ExPEC infections, assuming coverage of subportions of the non-typeable strains. See, e.g., Tables 1A-1C below. In both UTI and bacteremia target populations, serotypes O1, O2, O6, and O25 were identified as the four most prevalent E. coli serotypes, among which, serotype O25 was the most prevalent E. coli serotype in the bacteremia. It was also found that, for an O antigen serotype that is composed of distinct, yet structurally and antigenically related subtypes, one subtype may be more prevalent among the clinical isolates than the others. For example, O1A, O6A and O25B antigens were determined to be the more frequent subtypes among the analyzed more recent clinical strains or isolates for O1, O6 and O25 serotypes, respectively. See related disclosure on epidemiology studies in International Patent application No. PCT/EP2015/053739, the disclosure of which is herein incorporated by reference in its entirety.

TABLE 1A

Distribution of the most common UTI-associated E. coli serotypes from a collection of 1841 urine samples collected in Switzerland in 2012. Shown is the serotype distribution of samples from a relevant subpopulation of 671 subjects, and the distribution from all ** samples.
Most prevalent E. coli serotypes associated with UTI

| O-serotype | Community acquired UTI in 18-70 years old* (n = 671) | O-serotype | Community and hospital acquired UTI in all ages ** (n = 1871) |
|---|---|---|---|
| 6  | 10.75% | 2  | 8.75% |
| 2  | 9.55%  | 6  | 8.47% |
| 25 | 6.87%  | 25 | 8.37% |
| 1  | 5.52%  | 75 | 4.56% |
| 4  | 5.37%  | 1  | 4.29% |
| 75 | 4.78%  | 8  | 3.86% |
| 8  | 3.43%  | 18 | 3.53% |
| 18 | 3.28%  | 4  | 3.26% |
| 15 | 3.28%  | 15 | 2.39% |
| 73 | 2.24%  | 73 | 2.17% |
| 16 | 2.24%  | 16 | 1.85% |
| 7  | 1.94%  | 7  | 1.68% |

TABLE 1B

Prevalence of most common UTI-associated serotypes from selected literature ranging from 1987-2011 and from retrospectively analyzed US data from 2000-2011 (ECRC).

| INDICATION Serotype | TOTAL UTI available data from 1860 isolates | CYSTITIS available data from 1089 isolates | PYELONEPHRITIS available data from 373 isolates | US 2000-2010 315 (all UTI specimen except fecal, all ages, F + M)* |
|---|---|---|---|---|
| O1 | 4.8% | 4.1% | 5.4%  | 7.0%  |
| O2 | 7.1% | 4.9% | 15.3% | 14.0% |

TABLE 1B-continued

Prevalence of most common UTI-associated serotypes from selected literature ranging from 1987-2011 and from retrospectively analyzed US data from 2000-2011 (ECRC).

| INDICATION Serotype | TOTAL UTI available data from 1860 isolates | CYSTITIS available data from 1089 isolates | PYELONEPHRITIS available data from 373 isolates | US 2000-2010 315 (all UTI specimen except fecal, all ages, F + M)* |
|---|---|---|---|---|
| O4 | 7.8% | 6.0% | 3.2% | 3.2% |
| O6 | 16.9% | 16.3% | 7.8% | 18.7% |
| O7 | 3.3% | 2.4% | 2.4% | 1.9% |
| O8 | 1.7% | 3.2% | 0.8% | 3.5% |
| O15 | 0.6% | 1.5% | 0.8% | 1.3% |
| O16 | 4.3% | 3.2% | 7.2% | 1.9% |
| O18 | 7.0% | 7.1% | 6.7% | 7.0% |
| O21 | Na | Na | Na | 1.3% |
| O22 | 0.6% | 0.6% | 0.5% | 0.0% |
| O25 | 3.0% | 4.8% | 0.5% | 8.6% |
| O75 | 7.5% | 6.0% | 8.6% | 3.8% |
| O83 | 1.9% | 0.7% | 0.5% | 1.3% |
| O20 | | | | 1.6% |
| O77 | | | | 2.2% |
| O82 | | | | 1.9% |
| others and non typeable/not available | 33.3% | 39.2% | 40.2% | |
| other O-types (NT not available) | | | | 21.0% |

*Number of non-typeable was not available

TABLE 1C

Distribution of the most common bacteremia-associated E. coli O-serotypes from a collection of 860 blood isolates collected in the US and EU in the period 2011-2013. Indicated is the relative O-serotype distribution of the samples.

| O-serotype | Bacteremia in ≥60 years old US/EU 2011-2013 (n = 860) |
|---|---|
| 25 | 19.2 |
| 2 | 8.8 |
| 6 | 8.3 |
| 1 | 7.8 |
| 75 | 3.3 |
| 4 | 2.8 |
| 16 | 2.7 |
| 18 | 2.7 |
| 15 | 2.3 |
| 8 | 2.0 |
| 153 | 1.6 |
| 73 | 1.6 |

A novel O25 agglutinating clone has recently emerged in *E. coli* isolated from hospital settings, and this is named O25B. For O-serotype O25, it was found using subtyping analysis by PCR that the vast majority is actually of the O25B subtype (in a study of 24 tested clinical isolates with an O25 agglutination positive phenotype, 20 were assigned to the O25B subtype while the remaining 4 were assigned to the O25A subtype, and in the bacteremia population that was studied then, 56 of 57 studied O25 serotype isolates were typeable as O25B). It has been confirmed that autologous antisera recognize the autologous antigen better than the non-autologous antigen, and therefore inclusion of the O25B antigen into a vaccine can provide better protection against the predominant O25B clinical strains of the O25 group than inclusion of the O25A antigen would do (see, e.g., International Patent application No. PCT/EP2015/053739). Results showed that an O25B vaccine can give rise to sera that cross-react with an O25A antigen, thus also providing immune response against O25A serotype (Id.). Compositions according to embodiments of the invention comprise an *E. coli* O25B antigen conjugated to an EPA carrier protein and other *E. coli* O-antigens conjugated to the EPA carrier protein.

Compositions Comprising *E. coli* O Antigen Conjugates

In one general aspect, the invention relates to a multivalent vaccine containing O-antigen serotypes found predominantly among *E. coli* clinical isolates, which can be used to provide active immunization for the prevention of disease caused by ExPEC having the O-antigen serotypes contained in the vaccine. In one embodiment, the invention relates to a composition comprising an *E. coli* O25B antigen at a first concentration of 8 to 48 µg/ml, and at least one additional *E. coli* O-antigen at a second concentration that is 10% to 100% of the first concentration, wherein each of the *E. coli* O25B antigen and the at least one additional *E. coli* O-antigen is independently covalently bound to an EPA carrier protein.

Preferably, the at least one additional *E. coli* O antigen used in compositions according to embodiments of the invention is prevalent among the *E. coli* clinical isolates. Examples of such additional O antigens include, but are not limited to, *E. coli* O1, O2, O4, O6, O7, O8, O15, O16, O18, O21, O73, O75 and O153 antigens. Depending on the need, the composition can include more than one additional *E. coli* O antigens, such as two, three, four, five, six, seven, eight or nine additional *E. coli* O antigens, to provide immune protection against multiple *E. coli* serotypes in addition to *E. coli* O25B serotype. In a preferred embodiment, the additional *E. coli* O-antigen is selected from the group consisting of *E. coli* O1, O2 and O6 antigens. More preferably, the additional *E. coli* O-antigen is selected from the group consisting of *E. coli* O1A, O2 and O6A antigens.

In one embodiment, a composition of the invention comprises an *E. coli* O25B antigen at a first concentration of 10 to 36 µg/ml, and *E. coli* O1A, O2 and O6A antigens each at a concentration that is independently 10% to 100% of the first concentration, wherein each of the *E. coli* O25B antigen and the additional *E. coli*-antigens is independently covalently bound to an EPA carrier protein. In a preferred embodiment, each of the *E. coli* O1A, O2 and O6A antigens is independently present at a concentration of at least 5 µg/ml, more preferably, at a concentration of least 8 µg/ml.

A composition according to an embodiment of the invention contains *E. coli* O25B antigen at a concentration that is same or higher than the concentration of any of the additional O antigens in the composition. For example, the composition can have *E. coli* O25B antigen at a first concentration of, e.g., 10, 16, 24, 32 or 36 µg/ml, and one or more additional *E. coli* O-antigens each at a concentration that is, e.g. 10%, 20%, 30%, 40%, 50%, 60%, 70%, 80%, 90% or 100% of the first concentration. When the composition contains more than one additional O antigen, all of the additional O antigens can have the same concentration that is 10 to 100% of the *E. coli* O25B antigen concentration in the composition. Alternatively, the additional O antigens can also have different concentrations, each of which is independently 10-100% of the *E. coli* O25B antigen concentration. Preferably, the composition comprises 32 µg/ml *E. coli* O25B antigen and independently 16 to 32 µg/ml each of the one or more additional O antigens, wherein each of the *E. coli* O25B antigen and the additional *E. coli* O-antigens is independently covalently bound to an EPA carrier protein. In another preferred embodiment, the composition comprises 16 µg/ml *E. coli* O25B antigen, and independently 8 µg/ml to 16 µg/ml of each of the one or more additional O antigens, wherein each of the *E. coli* O25B antigen and the additional *E. coli* O-antigens is independently covalently bound to an EPA carrier protein.

In one preferred embodiment, the invention relates to a composition comprising an *E. coli* O25B antigen at a first concentration of 10 to 36 µg/ml, and a second concentration of each of an *E. coli* O1A antigen, an *E. coli* O2 antigen and an *E. coli* O6A antigen, wherein each of the *E. coli* O25B, O1A, O2 and O6A antigens are independently covalently bound to an EPA carrier protein, and the ratio of the first concentration to the second concentration is 1:1 to 2:1.

Preferably, the composition comprises the *E. coli* O25B, O1A, O2 and O6A antigens at a weight ratio of 1:1:1:1 or 2:1:1:1, and the composition comprises 32 µg/ml of the *E. coli* O25B antigen, wherein each of the O-antigen is covalently bound to an EPA carrier protein. In another preferred embodiment, the composition comprises the *E. coli* O25B, O1A, O2 and O6A antigens at a weight ratio of 1:1:1:1 or 2:1:1:1, and the composition comprises 16 µg/ml of the *E. coli* O25B antigen, wherein each of the O-antigen is covalently bound to an EPA carrier protein. More preferably, each of the *E. coli* O25B, O1A, O2 and O6A antigens are independently covalently bound to an EPA carrier protein having the amino acid sequence of SEQ ID NO: 1, and each of the O-antigen and EPA carrier protein conjugate is made in a cell, i.e., being a bioconjugate. Most preferably, the *E. coli* O25B, O1A, O2 and O6A antigens comprise, respectively, the structures of formula O25B', formula O1A', formula O2' and formula O6A' described infra.

The compositions described herein are useful in the treatment and prevention of infection of subjects (e.g., human subjects) with ExPEC. In certain embodiments, in addition to comprising *E. coli* O-antigens covalently bound to an EPA carrier protein, the compositions described herein comprise a pharmaceutically acceptable carrier. As used herein, the term "pharmaceutically acceptable" means approved by a regulatory agency of a Federal or a state government or listed in the U.S. Pharmacopeia or other generally recognized pharmacopeia for use in animals, and more particularly in humans. The term "carrier," as used herein in the context of a pharmaceutically acceptable carrier, refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin.

In a specific embodiment, provided herein is a composition comprising an *E. coli* O25B antigen covalently bound to an EPA carrier protein, and one or more additional *E. coli* O antigens each covalently bound to the EPA carrier protein.

In another specific embodiment, provided herein is a composition comprising (i) a bioconjugate comprising an *E. coli* O25B antigen covalently bound to an EPA carrier protein, and (ii) a bioconjugate comprising an *E. coli* O1A antigen covalently bound to an EPA carrier protein.

In another specific embodiment, provided herein is a composition comprising (i) a bioconjugate comprising an *E. coli* O25B antigen covalently bound to an EPA carrier protein, and (ii) a bioconjugate comprising an *E. coli* O2 antigen covalently bound to an EPA carrier protein.

In another specific embodiment, provided herein is a composition comprising (i) a bioconjugate comprising an *E. coli* O25B antigen covalently bound to an EPA carrier protein, and (ii) a bioconjugate comprising an *E. coli* O6A antigen covalently bound to an EPA carrier protein.

In another specific embodiment, provided herein is a composition comprising an *E. coli* O25B bioconjugate comprising an *E. coli* O25B antigen covalently bound to an EPA carrier protein, and two or more bioconjugates selected from the group consisting of: (i) an *E. coli* O1A bioconjugate comprising an *E. coli* O1A antigen covalently bound to an EPA carrier protein; (ii) an *E. coli* O2 bioconjugate comprising an *E. coli* O2 antigen covalently bound to an EPA carrier protein; and (iii) an *E. coli* O6A bioconjugate comprising an *E. coli* O6A antigen covalently bound to an EPA carrier protein.

In another specific embodiment, a composition provided herein comprises: (i) an *E. coli* O25B bioconjugate comprising an *E. coli* O25B antigen covalently bound to an EPA carrier protein; (ii) an *E. coli* O1A bioconjugate comprising an *E. coli* O1A antigen covalently bound to an EPA carrier protein; (iii) an *E. coli* O2 bioconjugate comprising an *E. coli* O2 antigen covalently bound to an EPA carrier protein; and (iv) an *E. coli* O6A bioconjugate comprising an *E. coli* O6A antigen covalently bound to an EPA carrier protein, wherein (i), (ii), (iii), and (iv) are formulated in a single formulation.

In another specific embodiment, a composition provided herein comprises: (i) an *E. coli* O25B bioconjugate comprising an *E. coli* O25B antigen covalently bound to an EPA carrier protein; (ii) an *E. coli* O1A bioconjugate comprising an *E. coli* O1A antigen covalently bound to an EPA carrier protein; (iii) an *E. coli* O2 bioconjugate comprising an *E. coli* O2 antigen covalently bound to an EPA carrier protein; and (iv) an *E. coli* O6A bioconjugate comprising an *E. coli* O6A antigen covalently bound to an EPA carrier protein, wherein (i), (ii), (iii), and (iv) are formulated in individual compositions that are administered in combination according to a method of an embodiment of the invention.

In certain embodiments, the foregoing compositions optionally comprise an EPA carrier protein covalently linked to an *E. coli* O-antigen other than *E. coli* O1A, O2, O6A, and O25B. Other *E. coli* O antigens include, but are not limited to, the additional O antigens listed in Tables 1A-1C above.

The compositions provided herein can be used for eliciting an immune response in a host to whom the composition is administered, i.e., are immunogenic. Thus, the compositions described herein can be used as vaccines against ExPEC infection, and can comprise any additional components suitable for use in a vaccine. In a specific embodiment, the compositions described herein are multivalent formulations, e.g., at least tetravalent formulations comprising bioconjugates of *E. coli* O-antigens of the O25B, O1A, O6A, and O2 serotypes/subserotypes.

In certain embodiments, the compositions described herein additionally comprise a preservative, such as the mercury derivative thimerosal. In a specific embodiment, the pharmaceutical compositions described herein comprise 0.001% to 0.01% thimerosal. In other embodiments, the pharmaceutical compositions described herein do not comprise a preservative.

In certain embodiments, the compositions described herein (e.g., the immunogenic compositions) comprise, or are administered in combination with, an adjuvant. The adjuvant for administration in combination with a composition described herein may be administered before, concomitantly with, or after administration of said composition. In some embodiments, the term "adjuvant" refers to a compound that when administered in conjunction with or as part of a composition described herein augments, enhances and/or boosts the immune response to a bioconjugate, but when the adjuvant compound is administered alone does not generate an immune response to the bioconjugate. In some embodiments, the adjuvant generates an immune response to the poly bioconjugate peptide and does not produce an allergy or other adverse reaction. Adjuvants can enhance an immune response by several mechanisms including, e.g., lymphocyte recruitment, stimulation of B and/or T cells, and stimulation of macrophages. In certain preferred embodiments, the compositions described herein do not comprise an adjuvant besides the bioconjugates, and/or are not administered in combination with an adjuvant besides the bioconjugates (in case the bioconjugates would comprise some intrinsic adjuvant properties, these would be disregarded and no extrinsic adjuvant would be added in these embodiments).

Specific examples of adjuvants include, but are not limited to, aluminum salts (alum) (such as aluminum hydroxide, aluminum phosphate, and aluminum sulfate), 3 De-O-acylated monophosphoryl lipid A (MPL) (see United Kingdom Patent GB2220211), MF59 (Novartis), AS03 (GlaxoSmithKline), AS04 (GlaxoSmithKline), polysorbate 80 (Tween 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al., in Vaccine Design: The Subunit and Adjuvant Approach (eds. Powell & Newman, Plenum Press, N Y, 1995); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., 1997, N. Engl. J. Med. 336, 86-91). Another adjuvant is CpG (Bioworld Today, Nov. 15, 1998).

In certain embodiments, the compositions described herein are formulated to be suitable for the intended route of administration to a subject. For example, the compositions described herein may be formulated to be suitable for subcutaneous, parenteral, oral, intradermal, transdermal, colorectal, intraperitoneal, and rectal administration. In a specific embodiment, the pharmaceutical composition may be formulated for intravenous, oral, intraperitoneal, intranasal, intratracheal, subcutaneous, intramuscular, topical, intradermal, transdermal or pulmonary administration. In certain embodiments, the compositions described herein are administered by intramuscular injection.

In certain embodiments, the compositions described herein additionally comprise one or more buffers, e.g., Tris-buffered saline, phosphate buffer, and sucrose phosphate glutamate buffer.

In certain embodiments, the compositions described herein additionally comprise one or more salts, e.g., Tris-hydrochloride, sodium chloride, calcium chloride, potassium chloride, sodium phosphate, monosodium glutamate, and aluminum salts (e.g., aluminum hydroxide, aluminum phosphate, alum (potassium aluminum sulfate), or a mixture of such aluminum salts). In one embodiment, a composition of the invention comprises the bioconjugates described herein in a Tris-buffered saline (TBS) pH 7.4 (e.g. containing Tris, NaCl and KCl, e.g. at 25 mM, 137 mM and 2.7 mM, respectively).

The compositions described herein can be included in a container, pack, or dispenser together with instructions for administration.

The compositions described herein can be stored before use, e.g., the compositions can be stored frozen (e.g., at about −20° C. or at about −70° C.); stored in refrigerated conditions (e.g., at about 4° C.); or stored at room temperature.

Methods/Uses

In another general aspect, the invention relates to a method of inducing an immune response to ExPEC in a subject in need thereof. Preferably, the immune response is effective to prevent or treat a disease associated with ExPEC in the subject in need thereof. The method comprises administering to the subject an *E. coli* O25B antigen at a first effective amount of 4 to 24 μg per administration, and at least one additional *E. coli* O antigen at a second effective amount that is 10% to 100% of the first effective amount, wherein each of the *E. coli* O25B antigen and the at least one additional *E. coli* O-antigen is independently covalently bound to an EPA carrier protein, and the composition is effective in inducing an immune response against the *E. coli* O25B antigen and the at least one additional *E. coli* O-antigen in the subject in need thereof.

Preferably, the at least one additional *E. coli* O antigen used in the methods and uses of the invention is prevalent among the *E. coli* clinical isolates. Examples of such additional O antigens include, but are not limited to, *E. coli* O1, O2, O4, O6, O7, O8, O15, O16, O18, O21, O73, O75 and O153 antigens. Depending on the need, more than one additional *E. coli* O antigens, such as two, three, four, five, six, seven, eight or nine additional *E. coli* O antigens, can be administered to provide immune protection against multiple *E. coli* serotypes in addition to *E. coli* O25B serotype.

In a preferred embodiment, a method of the invention induces an immune response in a subject in need thereof against ExPEC serotype O25, and one or more additional *E. coli* O-antigens selected from the group consisting of *E. coli* O1, O2 and O6 antigens. Preferably, a method of the invention induces an immune response in a subject in need thereof against ExPEC serotypes O25B, and one or more additional *E. coli* O-antigens selected from the group consisting of *E. coli* O1A, O2 and O6A antigens. The method comprises administering to a subject in need thereof an *E. coli* O25B antigen at a first effective amount of 5 to 18 μg per administration, and *E. coli* O1A, O2 and O6A antigens each at an effective amount that is independently 10% to 100% of the first effective amount, wherein each of the *E. coli* O25B antigen and the additional *E. coli* O-antigens is independently covalently bound to an EPA carrier protein. In a preferred embodiment, each of the *E. coli* O1A, O2 and O6A antigens is independently administered at an effective amount of at least 3 μg per administration, more preferably, at an effective amount of at least 4 μg per administration.

In a method according to an embodiment of the invention, the administered effective amount of *E. coli* O25B antigen is same or higher than the administered effective amount of any of the additional O antigens. For example, the *E. coli* O25B antigen can be administered at a first effective amount of 4 to 24 μg per administration, and the at least one additional *E. coli* O-antigen can be administered at a second effective amount that is, e.g., 10%, 20%, 30%, 40%, 50%, 60%, 70%, 80%, 90% or 100% of the first effective amount. When more than one additional O antigens are administered in combination, all of the additional O antigens can be administered at the same effective amount that is 10-100% of the first effective amount for the *E. coli* O25B antigen. The additional O antigens can also be administered at different effective amounts each of which is independently 10-100% of the first effective amount for the *E. coli* O25B antigen. Preferably, the *E. coli* O25B antigen is administered at the first effective amount of 5 μg to 18 μg, and the at least one additional O antigen is administered at a second effective amount that is independently 50% to 100% of the first effective amount.

In one embodiment according to the invention, a method of inducing an immune response to ExPEC in a subject in need thereof comprises administering to the subject an *E. coli* O25B antigen at a first effective amount of, e.g., 5, 6, 7, 8, 9, 10, 11, 12, 13, 14, 15 or 16 μg per administration, and *E. coli* O1A, O2 and O6A antigens each at an effective amount that is independently, e.g., 10%, 20%, 30%, 40%, 50%, 60%, 70%, 80%, 90% or 100% of the first effective amount, wherein each of the *E. coli* O25B antigen and the additional *E. coli* O-antigens is independently covalently bound to an EPA carrier protein.

In one preferred embodiment, the invention relates to a method of inducing an immune response to ExPEC in a subject in need thereof, comprising administering to the subject an *E. coli* O25B antigen at a first effective amount of 5 to 18 μg per administration, and a second effective amount of each of an *E. coli* O1A antigen, an *E. coli* O2 antigen and an *E. coli* O6A antigen, wherein each of the *E. coli* O25B, O1A, O2 and O6A antigens are independently covalently bound to an EPA carrier protein, and the ratio of the first effective amount to the second effective amount is 1:1 to 2:1. Preferably, the *E. coli* O25B, O1A, O2 and O6A antigens are administered to the subject at a dosage ratio of 1:1:1:1 or 2:1:1:1, and the *E. coli* O25B antigen is administered at 5 μg, 8 μg or 16 μg per administration. Also preferably, the *E. coli* O25B, O1A, O2 and O6A antigens are administered to the subject in one composition.

Provided herein are methods and uses of compositions of the invention for inducing an immune response to ExPEC in a subject in need thereof, comprising administering to the subject an *E. coli* O25B antigen covalently bound to an EPA carrier protein, and at least one additional *E. coli* O antigen covalently bound to the EPA carrier protein. In a specific embodiment, the compositions described herein are used to vaccinate a human subject to induce a protective immunity against ExPEC infection of the human subject.

Further provided herein are methods of inducing the production of opsonophagocytic antibodies against ExPEC in a subject in need thereof, comprising administering to the subject an *E. coli* O25B antigen covalently bound to an EPA carrier protein, and at least one additional *E. coli* O antigen covalently bound to the EPA carrier protein.

In one embodiment, said subject has an ExPEC infection at the time of administration. In another embodiment, said subject does not have an ExPEC infection at the time of administration. Examples of infections caused by ExPEC include, but are not limited to, urinary tract infection, surgical-site infection, bacteremia, abdominal or pelvic infection, pneumonia, nosocomial pneumonia, osteomyelitis, cellulitis, wound infection, meningitis, neonatal meningitis, peritonitis, cholangitis, soft-tissue infections, pyomyositis, septic arthritis, and sepsis. Preferably, the infection caused by ExPEC is an invasive ExPEC disease caused by ExPEC serotypes of which antigens are included in the compositions or methods according to embodiments of the invention.

The methods of inducing an immune response in a subject described herein result in vaccination of the subject against infection by the ExPEC strains whose O-antigens are present in the composition(s). When an O-antigen subtype is used, a method of the invention can also induce immune response to another O-antigen subtype having similar antigenicity.

In a specific embodiment, the immune response induced by a method or composition described herein is effective to prevent and/or treat an infection caused by *E. coli* of the O25 serotype. In a specific embodiment, said O25 serotype is O25B. In another specific embodiment, said O25 serotype is O25A.

In a specific embodiment, the immune response induced by a method or composition described herein is effective to prevent and/or treat an infection caused by *E. coli* of the O25 serotype, e.g. O25B serotype, and O1 serotype, e.g. O1A serotype.

In a specific embodiment, the immune response induced by a method or composition described herein is effective to prevent and/or treat an infection caused by *E. coli* of the O25 serotype, e.g. O25B serotype, and O2 serotype.

In a specific embodiment, the immune response induced by a method or composition described herein is effective to prevent and/or treat an infection caused by *E. coli* of the O25 serotype, e.g. O25B serotype, and O6 serotype, e.g. O6A serotype.

In a specific embodiment, the immune response induced by a method or composition described herein is effective to prevent and/or treat an infection caused by *E. coli* of the O25 serotype (e.g. O25B and/or O25A), and two or more of the following *E. coli* serotypes: O1 (e.g., O1A, Gln, and/or O1C), O2, and/or O6 (e.g., O6A and/or O6GlcNAc).

In a specific embodiment, the immune response induced by a method or composition described herein is effective to prevent and/or treat an infection caused by each of the following *E. coli* serotypes: O25 (e.g., O25B and/or O25A), O1 (e.g., O1A, O1B, and/or O1C), O2, and O6 (e.g., O6A and/or O6GlcNAc).

In a specific embodiment, the immune response induced by a method or composition described herein is effective to prevent and/or treat an infection caused by *E. coli* of the O25 serotype, e.g. O25B serotype, and an *E. coli* serotype other than O1, O2, O6, or O25, including, but not limited to, the additional O serotypes listed in Tables 1A-1C.

In order to immunize a subject against an ExPEC infection, the subject can be administered a single composition described herein, wherein said composition comprises *E. coli* O25B antigen, and one, two, three, four, or more additional *E. coli* O antigens described herein, each covalently bound to an EPA carrier protein. Alternatively, in order to treat a subject having an ExPEC infection or immunize a subject against an ExPEC infection, the subject can be administered multiple compositions described herein in combination. For example, a subject can be administered a composition comprising *E. coli* O25B antigen conjugated to an EPA carrier protein, in combination with the administration of two, three, four, or more compositions comprising additional O antigen conjugates according to embodiments of the invention.

In certain embodiments, the immune response induced in a subject following administration of a composition described herein is effective to prevent or reduce a symptom resulting from an ExPEC infection, preferably in at least 30%, more preferably at least 40%, such as at least 50%, of the subjects administered with the composition. Symptoms of ExPEC infection may vary depending on the nature of the infection and may include, but are not limited to: dysuria, increased urinary frequency or urgency, pyuria, hematuria, back pain, pelvic pain, pain while urinating, fever, chills, and/or nausea (e.g., in subjects having a urinary tract infection caused by ExPEC); high fever, headache, stiff neck, nausea, vomiting, seizures, sleepiness, and/or light sensitivity (e.g., in subjects having meningitis caused by ExPEC); fever, increased heart rate, increased respiratory rate, decreased urine output, decreased platelet count, abdominal pain, difficulty breathing, and/or abnormal heart function (e.g., in subjects having sepsis caused by ExPEC).

In certain embodiments, the immune response induced in a subject following administration of a composition described herein is effective to reduce the likelihood of hospitalization of a subject suffering from an ExPEC infection. In some embodiments, the immune response induced in a subject following administration of a composition described herein is effective to reduce the duration of hospitalization of a subject suffering from an ExPEC infection.

*E. coli* O-Antigens

Embodiments of the invention relate to compositions and methods relating to *E. coli* O25B antigen and one or more additional *E. coli* O antigens. Preferably, the additional O antigen is prevalent among the clinical isolates of *E. coli*. Examples of *E. coli* antigens that can be used in the invention include, but are not limited to, the *E. coli* O25B, O1A, O2, and O6A antigens.

As used herein an "*E. coli* O25B antigen" refers to an O antigen specific to the *E. coli* O25B serotype. In one embodiment, an *E. coli* O25B antigen comprises the structure of Formula O25B:

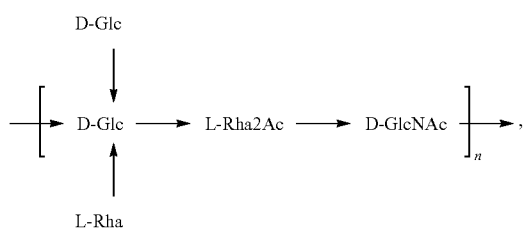

preferably, the *E. coli* O25B antigen comprises the structure of Formula O25B':

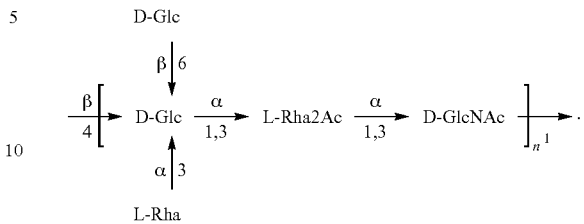

wherein the n in Formula O25B or Formula O25B' is an integer of 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20. In one embodiment of the invention, the n in Formula O25B or Formula O25B' is an integer of 10-20.

Preferably, a population of *E. coli* O25B antigens having the structure of Formula O25B, more preferably Formula O25B', is used in compositions and methods according to embodiments of the invention, wherein the n of at least 80% of the *E. coli* O25B antigens in the population is an integer of 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20. In one embodiment of the invention, the n of at least 80% of the *E. coli* O25B antigens in the population is an integer of 10-20.

As used herein, an "*E. coli* O1 antigen" refers to an O antigen specific to the *E. coli* O1 serotype. In one embodiment, an *E. coli* O1 antigen is an *E. coli* O1A antigen.

As used herein, an "*E. coli* O1A antigen" refers to an O antigen specific to the *E. coli* O1A serotype. In one embodiment, an *E. coli* O1A antigen comprises the structure of Formula O1A:

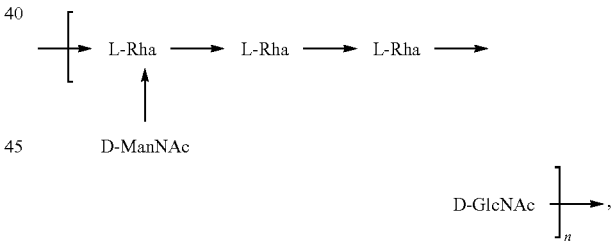

preferably, the *E. coli* O1A antigen comprises the structure of Formula O1A':

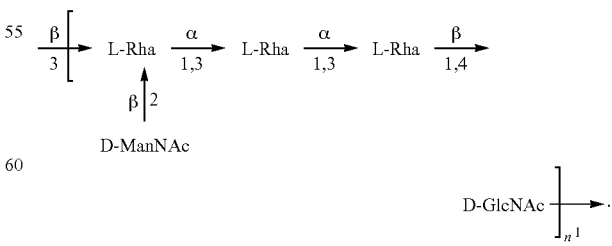

wherein the n in Formula O1A or Formula O1A' is an integer of 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20. In one embodiment, the n in Formula O1A or Formula O1A' is an integer of 7-15.

Preferably, a population of *E. coli* O1A antigens having the structure of Formula O1A, more preferably Formula O1A', is used in compositions and methods according to embodiments of the invention, wherein the n of at least 80% of the *E. coli* O1A antigens in the population is of 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20. In one embodiment, the n of at least 80% of the *E. coli* O1A antigens in the population is an integer of 5-15.

As used herein, an "*E. coli* O2 antigen" refers to an O antigen specific to the *E. coli* O2 serotype. In one embodiment, an *E. coli* O2 antigen comprises the structure of Formula O2:

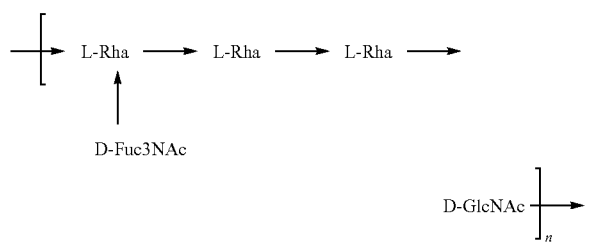

preferably, the *E. coli* O2 antigen comprises the structure of Formula O2':

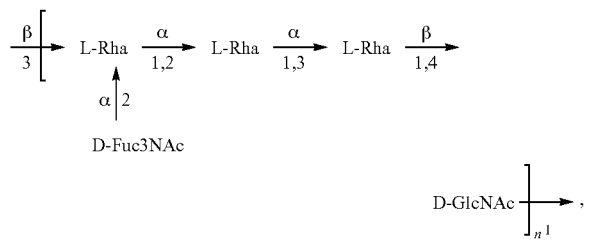

wherein the n in Formula O2 or Formula O2' is an integer of 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20. In one embodiment, the n in Formula O2 or Formula O2' is an integer of 8-16.

Preferably, a population of *E. coli* O2 antigens having the structure of Formula O2, more preferably Formula O2', is used in compositions and methods according to embodiments of the invention, wherein the n of at least 80% of the *E. coli* O2 antigens in the population is of 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20. In one embodiment, the n of at least 80% of the *E. coli* O2 antigens in the population is an integer of 5-20.

As used herein, an "*E. coli* O6 antigen" refers to an O antigen specific to the *E. coli* O6 serotype. In one embodiment, an *E. coli* O6 antigen is an *E. coli* O6A.

As used herein, an "*E. coli* O6A antigen," also referred to as "*E. coli* O6K2 antigen" or "*E. coli* O6Glc antigen," refers to an O antigen specific to the *E. coli* O6A serotype. In one embodiment, an *E. coli* O6A antigen comprises the structure of Formula O6A:

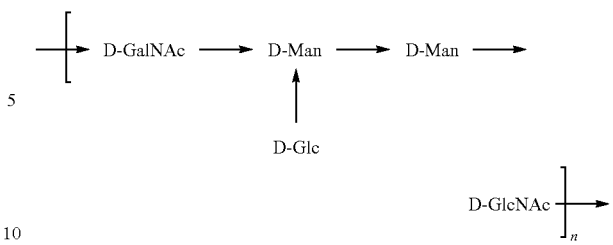

preferably, the *E. coli* O6A antigen comprises the structure of Formula O6A'.

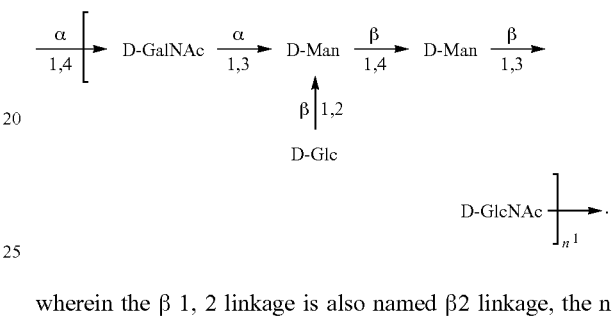

wherein the β 1, 2 linkage is also named β2 linkage, the n in Formula O6A or Formula O6A' is an integer of 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20. In one embodiment, the n in Formula O6A or Formula O6A' is an integer of 8-18.

Preferably, a population of *E. coli* O6A antigens having the structure of Formula O6A, more preferably Formula O6A', is used in compositions and methods according to embodiments of the invention, wherein the n of at least 80% of the *E. coli* O6A antigens in the population is of 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20. In one embodiment, the n of at least 80% of the *E. coli* O6A antigens in the population is an integer of 5-20.

In a preferred embodiment, a composition of the invention comprises *E. coli* O25B antigens having the structure of formula O25B', wherein the n of at least 80% of the *E. coli* O25B antigens in the population is an integer of 10-20; *E. coli* O1A antigens having the structure of formula O1A', wherein the n of at least 80% of the *E. coli* O1A antigens in the population is an integer of 5-15; *E. coli* O2 antigens having the structure of formula O2', wherein the n of at least 80% of the *E. coli* O2 antigens in the population is an integer of 5-20; and *E. coli* O6A antigens having the structure of formula O6A', wherein the n of at least 80% of the *E. coli* O6A antigens in the population is an integer of 5-20, wherein each of the O-antigens is covalently bound to an EPA carrier protein having the amino acid sequence of SEQ ID NO:1.

An *E. coli* O antigen useful in the invention can be produced by methods known in the art in view of the present disclosure. For example, they can be produced from a cell, preferably a recombinant cell that is optimized for the biosynthesis of the O antigen. See, e.g., relevant disclosure on the nucleic acids, proteins, host cells, production methods, etc., for *E. coli* O antigen biosynthesis in WO 2006/119987, WO 2009/104074, International Patent Application No. PCT/EP2015/053739, Ihssen et al., 2010, *Microbial Cell Factories* 9, 61, the disclosures of which are herein incorporated by reference in their entirety.

EPA Carrier Protein

According to embodiments of the invention, each *E. coli* O antigen is covalently bound to an EPA carrier protein (see, e.g., Ihssen et al., 2010, *Microbial Cell Factories* 9, 61). Various detoxified EPA variants have been described in literature and can be used as EPA carrier proteins in the conjugates described herein.

In certain embodiments, the EPA carrier proteins used in the conjugates described herein are EPAs modified in such a way that the protein is less toxic and/or more susceptible to glycosylation. For example, detoxification can be achieved by mutating and deleting the catalytically essential residues, such as L552V and ΔE553, according to Lukac et al., *Infect Immun*, 56: 3095-3098, 1988 and Ho et al., *Hum Vaccin*, 2:89-98, 2006. In a specific embodiment, the carrier proteins used in the generation of the conjugates described herein are EPAs modified such that the number of glycosylation sites in the carrier proteins is optimized in a manner that allows for lower concentrations of the protein to be administered, e.g., in an immunogenic composition, in its bioconjugate form.

In certain embodiments, the EPA carrier proteins are EPAs modified to include 1, 2, 3, 4, 5, 6, 7, 8, 9, 10, or more glycosylation sites than would normally be associated with the carrier protein (e.g., relative to the number of glycosylation sites associated with the carrier protein in its native/natural, e.g., "wild-type" state). In specific embodiments, introduction of glycosylation sites is accomplished by insertion of glycosylation consensus sequences (e.g., Asn-X-Ser(Thr), wherein X can be any amino acid except Pro (SEQ ID NO: 2); or preferably Asp(Glu)-X-Asn-Z-Ser(Thr), wherein X and Z are independently selected from any natural amino acid except Pro (SEQ ID NO:3) (see WO 2006/119987)) anywhere in the primary structure of the EPA protein. In one particular embodiment, the EPA carrier protein comprises 4 consensus glycosylation sequences Asp/Glu-X-Asn-Z-Ser/Thr (SEQ ID NO: 3), and has an amino acid sequence as provided in SEQ ID NO: 1.

In certain embodiments, the EPA carrier protein can be produced together with a signal sequence (such as a signal peptide for *E. coli* DsbA, *E. coli* outer membrane porin A (OmpA), *E. coli* maltose binding protein (MalE), etc.) that targets the carrier protein to the periplasmic space of the host cell that expresses the carrier protein. The EPA carrier protein can also be modified to a "tag," i.e., a sequence of amino acids that allows for the isolation and/or identification of the carrier protein.

An EPA carrier protein useful in the invention can be produced by methods known in the art in view of the present disclosure. See, e.g., relevant disclosure in e.g., Ihssen et al., 2010, *Microbial Cell Factories* 9, 61, and in WO 2006/119987, WO 2009/104074, and International Patent application No. PCT/EP2015/053739, the disclosure of which are herein incorporated by reference in their entirety.

Conjugates

In certain embodiments, a host cell can produce an *E. coli* O antigen and an EPA carrier protein, and covalently bind the O antigen to the EPA carrier protein to form a bioconjugate useful in the invention. See, e.g., relevant disclosure in e.g., Ihssen et al., 2010, *Microbial Cell Factories* 9, 61, and in WO 2006/119987, WO 2009/104074, and International Patent application No. PCT/EP2015/053739, the disclosures of which are herein incorporated by reference in their entirety.

Alternatively, the glycoconjugates can be prepared by chemical synthesis, i.e., prepared outside of host cells (in vitro). For example, the *E. coli* O-antigens described herein, e.g., O25B antigen, can be conjugated to carrier proteins using methods known to those of skill in the art, including by means of using activation reactive groups in the polysaccharide/oligosaccharide as well as the protein carrier. See, e.g., Pawlowski et al., 2000, *Vaccine* 18:1873-1885; and Robbins et al., 2009, *Proc Natl Acad Sci USA* 106:7974-7978, the disclosures of which are herein incorporated by reference. Such approaches comprise extraction of antigenic polysaccharides/oligosaccharides from host cells, purifying the polysaccharides/oligosaccharides, chemically activating the polysaccharides/oligosaccharides, and conjugating the polysaccharides/oligosaccharides to a carrier protein.

Bioconjugates have advantageous properties over glycoconjugates made in vitro, e.g., bioconjugates require less chemicals in manufacture and are more consistent and homogenous in terms of the final product generated. Thus, bioconjugates are preferred over chemically produced glycoconjugates.

In a specific embodiment, the EPA carrier protein is N-linked to an *E. coli* O-antigen useful in the invention. For example, the *E. coli* O antigen is linked to the Asn residue in a glycosylation sequence of a carrier protein, such as Asn-X-Ser(Thr), wherein X can be any amino acid except Pro (SEQ ID NO: 2), preferably Asp(Glu)-X-Asn-Z-Ser(Thr), wherein X and Z are independently selected from any natural amino acid except Pro (SEQ ID NO: 3).

The conjugates described herein can be purified by any method known in the art for purification of a protein, for example, by chromatography (e.g., ion exchange, anionic exchange, affinity, and sizing column chromatography), centrifugation, differential solubility, or by any other standard technique for the purification of proteins. See, e.g., Saraswat et al., 2013, *Biomed. Res.* Int. ID #312709 (p. 1-18); see also the methods described in WO 2009/104074. The actual conditions used to purify a particular conjugate will depend, in part, on the synthesis strategy (e.g., synthetic production vs. recombinant production) and on factors such as net charge, hydrophobicity, and/or hydrophilicity of the bioconjugate, and will be apparent to those having skill in the art.

Combination Therapies

In certain embodiments, a composition described herein is administered to a subject in combination with one or more other therapies (e.g., antibacterial or immunomodulatory therapies). The one or more other therapies can be beneficial in the treatment or prevention of an ExPEC infection or can ameliorate a symptom or condition associated with an ExPEC infection. In some embodiments, the one or more other therapies are pain relievers or anti-fever medications. In certain embodiments, the therapies are administered less than 5 minutes apart to less than 1 week apart. Any antibacterial agents known to one of skill in the art (e.g. antibiotics) may be used in combination with a composition described herein.

Patient Populations

In certain embodiments, a composition (or method) described herein is administered (or applied) to a naïve subject, i.e., a subject that does not have an ExPEC infection or has not previously had an ExPEC infection. In one embodiment, a composition (or method) described herein is administered (or applied) to a naïve subject that is at risk of acquiring an ExPEC infection.

In certain embodiments, a composition (or method) described herein is administered (or applied) to a subject who has been or was previously diagnosed with an ExPEC infection. In some embodiments, a composition (or method) described herein is administered (or applied) to a subject infected with ExPEC before symptoms manifest or symptoms become severe (e.g., before the patient requires hospitalization).

In certain embodiments, a composition (or method) described herein is administered (or applied) to a subject who has been diagnosed with an uropathogenic *E. coli* (UPEC) infection. In some embodiments, a composition (or method) described herein is administered (or applied) to a subject suffering from reoccurring urinary tract infections. In some embodiments, a composition (or method) described herein is administered (or applied) to a subject suffering from reoccurring urinary tract infections, but is healthy at the moment of treatment. In some embodiments, a composition (or method) described herein is administered (or applied) to a subject having or at risk of acquiring bacteremia or sepsis.

In some embodiments, a subject to be administered (or applied) a composition (or method) described herein is an animal. In certain embodiments, the animal is a canine. In certain embodiments, the animal is a feline. In certain embodiments, the animal is a horse. In certain embodiments, the animal is a cow. In certain embodiments, the animal is a mammal, e.g., a horse, swine, rabbit, mouse, or primate. In a preferred embodiment, the subject is a human.

In certain embodiments, a subject to be administered (or applied) a composition (or method) described herein is a human subject, preferably, a human subject at risk of having an invasive ExPEC disease. In certain embodiments, a subject to be administered (or applied) a composition (or method) described herein is a human adult more than 50 years old. In certain embodiments, a subject to be administered (or applied) a composition (or method) described herein is a human adult more than 55, more than 60 or more than 65 years old.

In certain embodiments, a subject to be administered (or applied) a composition (or method) described herein is a human child. In certain embodiments, a subject to be administered (or applied) a composition (or method) described herein is a human child. In certain embodiments, a subject to be administered (or applied) a composition (or method) described herein is a human infant, including a premature human infant. In some embodiments, a subject to be administered (or applied) a composition (or method) described herein is a human toddler. In certain embodiments, a subject to be administered (or applied) a composition (or method) described herein is not an infant of less than 6 months old.

In certain embodiments, a subject to be administered (or applied) a composition (or method) described herein is an individual who is pregnant. In certain embodiments, a subject to be administered (or applied) a composition (or method) described herein is a woman who has given birth 1, 2, 3, 4, 5, 6, 7, or 8 weeks earlier.

In certain embodiments, a subject to be administered (or applied) a composition (or method) described herein is an individual at increased risk of ExPEC, e.g., an immunocompromised or immunodeficient individual, an individual scheduled for surgery or recently undergone a surgery, an individual having a wound injury, an intensive care unit (ICU) or critical care unit (CCU) patient, etc. In certain embodiments, a subject to be administered (or applied) a composition (or method) described herein is an individual in close contact with an individual having or at increased risk of ExPEC infection.

In certain embodiments, a subject to be administered (or applied) a composition (or method) described herein is a health care worker. In certain embodiments, a subject to be administered (or applied) a composition (or method) described herein is immunocompromised (e.g., suffers from HIV infection) or immunosuppressed.

In certain embodiments, a subject to be administered (or applied) a composition (or method) described herein has diabetes. In certain embodiments, a subject to be administered (or applied) a composition (or method) described herein has multiple sclerosis.

In certain embodiments, a subject to be administered (or applied) a composition (or method) described herein has a condition that requires them to use a catheter, such as a urinary catheter. In certain embodiments, a subject to be administered (or applied) a composition (or method) described herein has a spinal cord injury.

In certain embodiments, the subject is a male who will undergo or has recently undergone a prostate biopsy.

In a preferred embodiment, the subject to be administered (or applied) a composition (or method) described herein is an at-risk human adult in need of immunization for the prevention of invasive ExPEC disease caused by ExPEC serotypes O1A, O2, O6A and O25B. Examples of at-risk human include, but are not limited to, those described herein supra. Other examples of at-risk human include, e.g., individuals having transrectal ultrasonography with prostate needle biopsy (TRUS-PNB) or recurrent urosepsis, residents of a long term care facility (LTCF), long term care (LTAC)-assisted living, pre-surgery patients (including but not limited to, patients scheduled for genito-urinary/abdominal surgery); pre-dialysis patients, pre-dialysis, etc.

Dosage and Frequency of Administration

Administration of the conjugates of O-antigens and an EPA carrier protein and/or composition thereof can be done via various routes known to the clinician, for instance subcutaneous, parenteral, intravenous, intramuscular, topical, oral, intradermal, transdermal, intranasal, etc. In one embodiment, administration is via intramuscular injection.

According to embodiments of the invention, the dosage level of *E. coli* O25B antigen covalently should be no less, preferably more, than the dosage levels of the other *E. coli* O antigens used in a composition or method of the invention, wherein each of the *E. coli* O antigens is covalently bound to an EPA carrier protein. The precise dosage to be employed in the formulation and method will depend on the route of administration, and the seriousness of the infection, and should be decided according to the judgment of the practitioner and each subject's circumstances.

In certain embodiments of the invention, exemplary dosages for *E. coli* O25B antigen range from 4 to 24 µg of O25B antigen per administration, and the exemplary dosages for each of the additional *E. coli* O antigens to be used in combination with the *E. coli* O25B antigen range from 10% to 100% of the dosage of *E. coli* O25B antigen, wherein each of the *E. coli* O antigens is covalently bound to an EPA carrier protein. In certain embodiments, an exemplary dosage for an *E. coli* O25B glycoconjugate is, e.g., 4, 5, 6, 7, 8, 9, 10, 11, 12, 13, 14, 15, 16, 17, 18, 19, 20, 21, 22, 23 or 24 µg of 25B antigen per administration, and an exemplary dosage for another *E. coli* O glycoconjugate to be used in combination with the *E. coli* O25B glycoconjugate is, e.g., 10%, 20%, 30%, 40%, 50%, 60%, 70%, 80%, 90% or 100% of the dosage for the *E. coli* O25B glycoconjugate, wherein the dosage is calculated by the amount of the O antigen in the O glycoconjugates per administration.

In certain embodiments of the invention, a subject in need thereof is administered with 0.5 ml of a composition according to the invention.

In certain embodiments, an exemplary dosage for per administration to a human subject corresponds to 0.5 ml of a composition containing a first concentration of about 8-48 µg/mL, e.g., about 8, 12, 16, 20, 24, 28, 32, 36, 40, 44 or 48 µg/mL, of E. coli O25B antigen covalently bound to an EPA carrier protein, and a concentration of 10% to 100% of the first concentration of one or more additional E. coli O antigens covalently bound to the EPA carrier protein.

In certain embodiments, an exemplary dosage for per administration to a human subject corresponds to 0.5 ml of a composition containing a concentration of about 16 µg/mL of E. coli O25B antigen covalently bound to an EPA carrier protein, about 8 µg/mL of E. coli O1A antigen covalently bound to an EPA carrier protein, about 8 µg/mL of E. coli O2 antigen covalently bound to an EPA carrier protein, and about 8 µg/mL of E. coli O6A antigen covalently bound to an EPA carrier protein.

In certain embodiments, an exemplary dosage for per administration to a human subject corresponds to 0.5 ml of a composition containing a concentration of about 16 µg/mL of E. coli O25B antigen covalently bound to an EPA carrier protein, about 16 µg/mL of E. coli O1A antigen covalently bound to an EPA carrier protein, about 16 µg/mL of E. coli O2 antigen covalently bound to an EPA carrier protein, and about 16 µg/mL of E. coli O6A antigen covalently bound to an EPA carrier protein.

In certain embodiments, an exemplary dosage for per administration to a human subject corresponds to 0.5 ml of a composition containing a concentration of about 32 µg/mL of E. coli O25B antigen covalently bound to an EPA carrier protein, about 16 µg/mL of E. coli O1A antigen covalently bound to an EPA carrier protein, about 16 µg/mL of E. coli O2 antigen covalently bound to an EPA carrier protein, and about 16 µg/mL of E. coli O6A antigen covalently bound to an EPA carrier protein.

In certain embodiments, an exemplary dosage for per administration to a human subject corresponds to 0.5 ml of a composition containing a concentration of about 32 µg/mL of E. coli O25B antigen covalently bound to an EPA carrier protein, about 32 µg/mL of E. coli O1A antigen covalently bound to an EPA carrier protein, about 32 µg/mL of E. coli O2 antigen covalently bound to an EPA carrier protein, and about 32 µg/mL of E. coli O6A antigen covalently bound to an EPA carrier protein.

In certain embodiments, E. coli O-antigen conjugates, preferably bioconjugates, described herein or a composition described herein is administered to a subject once as a single dose. In certain embodiments, E. coli O-antigen conjugates, preferably bioconjugates, described herein or a composition described herein is administered to a subject as a single dose followed by a second dose 3 to 6 weeks later. In accordance with these embodiments, booster inoculations can be administered to the subject at 6 to 24 month intervals following the second inoculation. In certain embodiments, the booster inoculations can utilize a different E. coli O-antigen, bioconjugate, or composition. In some embodiments, the administration of the same E. coli O-antigen conjugate, or composition can be repeated and the administrations can be separated by at least 1 day, 2 days, 3 days, 5 days, 7 days, 10 days, 15 days, 30 days, 45 days, 2 months, 75 days, 3 months, or at least 6 months. In certain embodiments, an E. coli O-antigen conjugate described herein or a composition described herein is administered to a subject as a single dose once per year. In certain embodiments, an E. coli O-antigen conjugate described herein or a composition described herein is administered to a subject as a single dose once per n years, n being for instance about 2, 3, 4, 5, 6, 7, 8, 9, 10, 15 or 20 years.

In certain embodiments, an E. coli O-antigen conjugate described herein or a composition described herein is administered to a subject as 2, 3, 4, 5 or more doses 2 weeks, 3 weeks, 4 weeks, 5 weeks or 6 weeks apart. In some embodiments, 2, 3, 4, 5 or more doses of an E. coli O-antigen conjugate described herein or a composition described herein are administered to a subject 2, 3, 4, 5 or 6 weeks apart. In certain embodiments, the E. coli O-antigen conjugate, or composition administered is the same each time. In certain embodiments, the E. coli O-antigen conjugate, or composition administered is different each time.

Assays

The ability of the conjugates/compositions described herein to generate an immune response in a subject can be assessed using any approach known to those of skill in the art in view of the present disclosure.

Assay for Assessing Ability of Bioconjugates to Induce an Immune Response

In some embodiments, the ability of a bioconjugate to generate an immune response in a subject can be assessed by immunizing a subject (e.g., a mouse) or set of subjects with the bioconjugate and immunizing an additional subject (e.g., a mouse) or set of subjects with a control (e.g., a placebo). The subjects or set of subjects can subsequently be challenged with ExPEC and the ability of the ExPEC to cause disease (e.g., UTI) in the subjects or set of subjects can be determined. Those skilled in the art will recognize that if the subject or set of subjects immunized with the control suffer(s) from disease subsequent to challenge with the ExPEC but the subject or set of subjects immunized with a bioconjugate(s) or composition thereof described herein suffer less from or do not suffer from disease, then the bioconjugate is able to generate an immune response in a subject. The ability of a bioconjugate(s) or composition thereof described herein to induce antiserum that cross-reacts with an O-antigen from ExPEC can be tested by, e.g., an immunoassay, such as an ELISA.

In Vitro Bactericidal Assays

The ability of the conjugates/compositions described herein to generate an immune response in a subject can be assessed using a serum bactericidal assay (SBA) or opsonophagocytotic killing assay (OPK), which represents an established and accepted method that has been used to obtain approval of glycoconjugate-based vaccines. Such assays are well-known in the art and, briefly, comprise the steps of generating and isolating antibodies against a target of interest (e.g., an O-antigen, e.g., O25B, of E. coli) by administering to a subject (e.g., a mouse) a compound that elicits such antibodies. Subsequently, the bactericidal capacity of the antibodies can be assessed by, e.g., culturing the bacteria in question (e.g., E. coli of the relevant serotype) in the presence of said antibodies and complement and—depending on the assay—neutrophilic cells and assaying the ability of the antibodies to kill and/or neutralize the bacteria, e.g., using standard microbiological approaches.

Kits

Provided herein is a pack or kit comprising one or more containers filled with one or more of the ingredients of the compositions described herein, such as one or more E. coli O antigens and/or conjugates of the E. coli O antigens covalently bound to an EPA carrier protein according to embodiments of the invention. Optionally associated with such container(s) can be a notice or instructions in the form prescribed by a governmental agency regulating the manufacture, use or sale of pharmaceuticals or biological products, which notice reflects approval by the agency of manufacture, use or sale for human administration. The kits encompassed herein can be used in the above methods of treatment and immunization of subjects.

The following examples of the invention are to further illustrate the nature of the invention. It should be understood that the following examples do not limit the invention and that the scope of the invention is to be determined by the appended claims.

Embodiments

Embodiment 1 is a composition comprising a first concentration of an *E. coli* O25B antigen polysaccharide, and a second concentration of each of an *E. coli* O1A antigen polysaccharide, an *E. coli* O2 antigen polysaccharide and an *E. coli* O6A antigen polysaccharide, wherein the ratio of the first concentration to the second concentration is 1:1 to 2:1, each of the *E. coli* O25B, O1A, O2 and O6A antigen polysaccharides are independently covalently bound to a detoxified exotoxin A of *Pseudomonas aeruginosa* (EPA) carrier protein, and the first concentration is 10 to 36 μg/ml.

Embodiment 2 is the composition of embodiment 1, comprising the *E. coli* O25B, O1A, O2 and O6A antigen polysaccharides at a weight ratio of 1:1:1:1.

Embodiment 3 is the composition of embodiment 1, comprising the O25B, O1A, O2 and O6A antigen polysaccharides at a weight ratio of 2:1:1:1.

Embodiment 4 is the composition of any one of embodiments 1 to 3, comprising 16 μg/ml of the O25B antigen polysaccharide.

Embodiment 5 is the composition of any one of embodiments 1 to 3, comprising 32 μg/ml of the O25B antigen polysaccharide.

Embodiment 6 is a multivalent immune composition comprising an *E. coli* O25B antigen polysaccharide at a first dose of 5 to 18 μg, and an *E. coli* O1A antigen polysaccharide, an *E. coli* O2 antigen polysaccharide and an *E. coli* O6A antigen polysaccharide each at a dose that is independently 50% to 100% of the first dose, wherein each of the *E. coli* O25B, O1A, O2 and O6A antigen polysaccharides are independently covalently bound to a detoxified exotoxin A of *Pseudomonas aeruginosa* (EPA) carrier protein.

Embodiment 7 is a multivalent immune composition comprising an *E. coli* O25B antigen polysaccharide having the structure of Formula O25B':

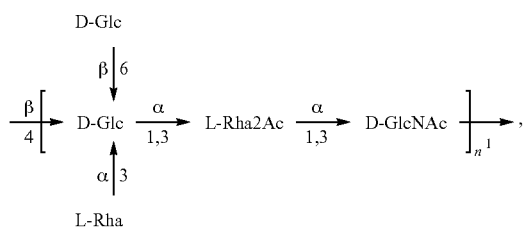

an *E. coli* O1A antigen polysaccharide having the structure of Formula O1A':

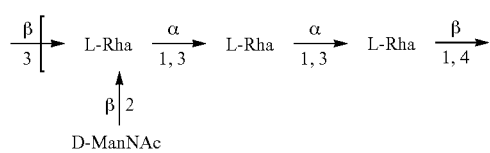

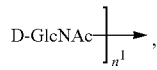

an *E. coli* O2 antigen polysaccharide having the structure of Formula O2':

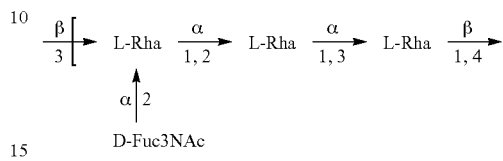

an *E. coli* O6A antigen polysaccharide having the structure of Formula O6A':

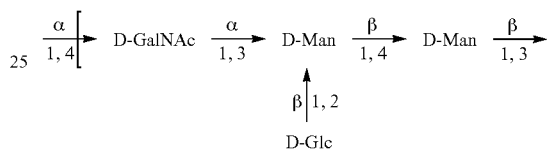

wherein n is independently an integer of 5 to 25, and each of the *E. coli* O25B, O1A, O2 and O6A antigen polysaccharides are independently covalently bound to a carrier protein having the amino acid sequence of SEQ ID NO:1; and the concentrations of the *E. coli* O25B, O1A, O2, O6A antigen polysaccharides in the compositions are respectively 16:8:8:8 μg/ml, 16:16:16:16 μg/ml, 32:16:16:16 μg/ml or 32:32:32:32 μg/ml.

Embodiment 8 is a method of inducing an immune response to extra-intestinal pathogenic *E. coli* (ExPEC) in a subject in need thereof, comprising administering to the subject a composition of any one of embodiments 1 to 7.

Embodiment 9 is a method of inducing an immune response to extra-intestinal pathogenic *E. coli* (ExPEC) in a subject in need thereof, comprising administering to the subject a first effective amount of an *E. coli* O25B antigen polysaccharide, and a second effective amount of each of an *E. coli* O1A antigen polysaccharide, an *E. coli* O2 antigen polysaccharide and an *E. coli* O6A antigen polysaccharide, wherein the ratio of the first effective amount to the second effective amount is 1:1 to 2:1, each of the *E. coli* O25B, O1A, O2 and O6A antigen polysaccharides are independently covalently bound to a detoxified exotoxin A of *Pseudomonas aeruginosa* (EPA) carrier protein, and the first effective amount is 5 to 18 μg per administration.

Embodiment 10 is the method of embodiment 9, wherein the *E. coli* O25B, O1A, O2 and O6A antigen polysaccharides are administered at a dosage ratio of 1:1:1:1.

Embodiment 11 is the method of embodiment 9, wherein the *E. coli* O25B, O1A, O2 and O6A antigen polysaccharides are administered at a dosage ratio of 2:1:1:1.

Embodiment 12 is the method of any one of embodiments 8 to 11, wherein 8 μg of the O25B antigen polysaccharide is administered per administration.

Embodiment 13 is the method of any one of embodiments 8 to 11, wherein 16 μg of the O25B antigen polysaccharide is administered per administration.

Embodiment 14 is the method of any one of embodiments 8 to 13, wherein the *E. coli* O25B, O1A, O2 and O6A antigen polysaccharides are administered together in one composition.

Embodiment 15 is a method of inducing an immune response to extra-intestinal pathogenic *E. coli* (ExPEC) in a subject in need thereof, comprising administering to the subject an *E. coli* O25B antigen polysaccharide having the structure of Formula O25B':

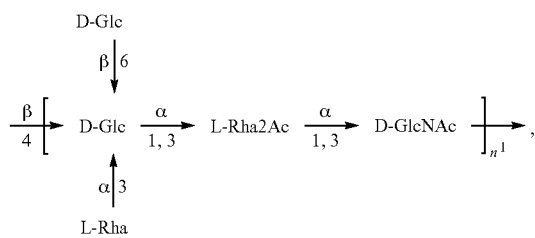

an *E. coli* O1A antigen polysaccharide having the structure of Formula O1A':

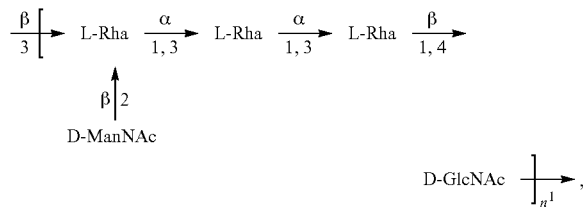

an *E. coli* O2 antigen polysaccharide having the structure of Formula O2':

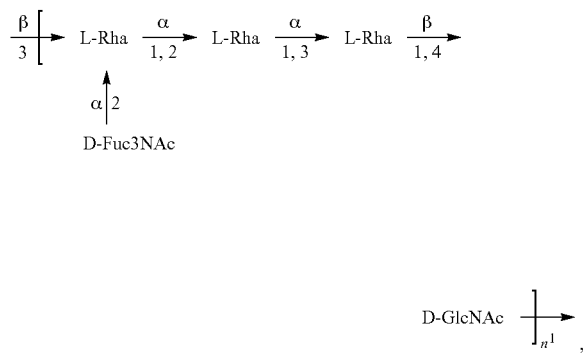

an *E. coli* O6A antigen polysaccharide having the structure of Formula O6A':

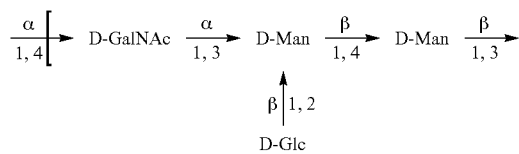

-continued

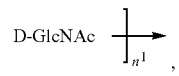

wherein n is independently an integer of 5 to 25, each of the *E. coli* O25B, O1A, O2 and O6A antigen polysaccharides are independently covalently bound to a carrier protein having the amino acid sequence of SEQ ID NO:1, and the *E. coli* O25B, O1A, O2 and O6A antigen polysaccharides are administered at 844:4 g, 8:8:8:8 μg, 16:8:8:8 μg or 16:16:16:16 μg per administration.

Embodiment 16 is the method of any one of embodiments 8 to 15, wherein the immune response limits the severity of or prevents an invasive ExPEC disease caused by ExPEC serotypes O1A, O2 and O6A and O25B in an at-risk human subject.

Embodiment 17 is the method of embodiment 16, wherein the adult human subject has or is at risk of having an invasive ExPEC disease selected from the group consisting of urinary tract infection, a surgical-site infection, an abdominal or pelvic infection, pneumonia, nosocomial pneumonia, osteomyelitis, cellulitis, sepsis, bacteremia, a wound infection, pyelonephritis, meningitis, neonatal meningitis, peritonitis, cholangitis, soft-tissue infections, pyomyositis and septic arthritis.

Embodiment 18 is a process of making a composition of any one of embodiments 1 to 7, comprising combining the *E. coli* O25B antigen polysaccharide, the *E. coli* O1A antigen polysaccharide, the *E. coli* O2 antigen polysaccharide and the *E. coli* O6A antigen polysaccharide to thereby obtain the composition.

Examples

O-Antigen Bioconjugates

Figure 2:
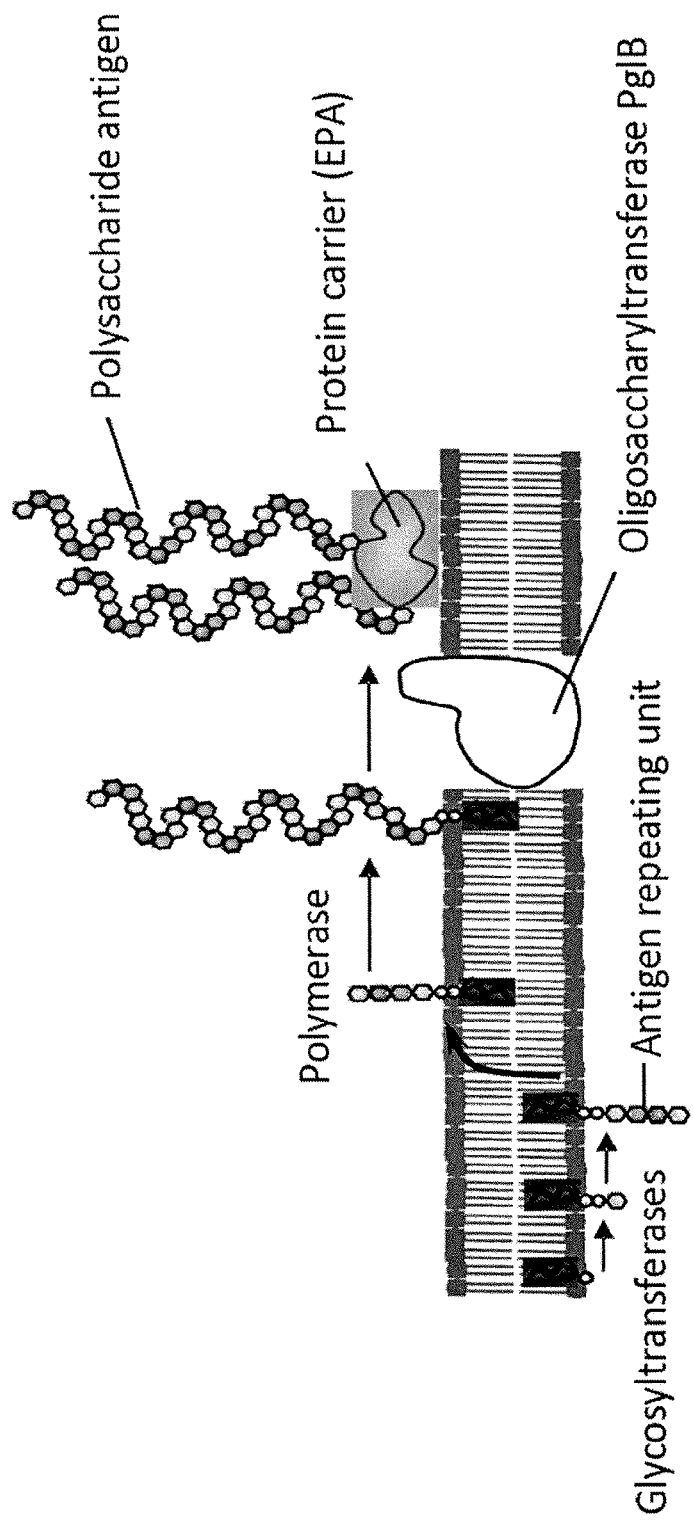
FIG. 2 is a detailed schematic representation of the protein glycosylation process.

O1A-EPA, O2-EPA, O6A-EPA and O25B-EPA bioconjugates containing, respectively, *E. coli* O1A, O2, O6A and O25B covalently linked to the glycosylation sites of an EPA protein carrier can be produced, purified, and characterized as described in, e.g., Ihssen et al., 2010, Microbial Cell Factories 9, 61, and in WO 2006/119987, WO 2009/104074, and International Patent application No. PCT/EP2015/053739, the disclosure of which are herein incorporated by reference in their entirety. The bioconjugates are synthesized using recombinant *E. coli* cells, which express the polysaccharide-synthesizing enzymes of the different O-serotypes in the presence of oligosaccharyltransferase PglB, and a protein carrier (EPA). In this approach, the glycoconjugate vaccine can be expressed in the periplasm of *E. coli*, extracted and purified through a biochemical process illustrated in FIG. 1 and FIG. 2. Table 2 indicates host strains used for the production of conjugates according to an embodiment of the invention.

TABLE 2

Host strains for production of preclinical, toxicology study and clinical batches

| Product | Strain | EPA expression plasmid | PglB expression plasmid |
|---|---|---|---|
| EPA-O1A | W3110 Δrfb::rfb(upec032) ΔwaaL | pGVXN1076 | pGVXN970 |
| EPA-O2 | W3110 Δrfb::rfb(upec116) ΔwaaL | pGVXN1076 | pGVXN971 |
| EPA-O6A | W3110 Δrfb::rfb(CCUG11309) ΔwaaL | pGVXN659 | pGVXN114 |
| EPA-O25B | W3110 Δrfb::rfb(upec138) ΔwaaL ΔgtrABS | pGVXN1076 | pGVXN970 |

For example, for O25B-EPA production, a strain with a genomically integrated O25B cluster was constructed: W3110 ΔwaaL ΔgtrABS ΔrJbO16::rfb(upec138), which was transformed with plasmids pGVXN1076 (which expresses the EPA having the amino acid sequence of SEQ ID NO:1) and pGVXN970 (which expressed the oligosaccharyl transferase PelB) (WO/2009/104074). This strain was constructed starting from strain W3110 by the methods of Datsenko and Wanner (2000, *Proc Natl Acad Sci USA* 97: 6640-6645) and a homologous recombination technique for site directed integration of large inserts into bacterial chromosomes (see WO 2014/057109). The rfb cluster related to the O25B antigen was cloned from *E. coli* strain upec138, which is positive for O25B. The recombinant host cells produced O25B/EPA bioconjugates in the periplasm. The resulting O25B bioconjugates were characterized using standard release and characterization assays. Bioconjugates were purified using two consecutive anionic exchange and size exclusion chromatography steps, yielding 98.1% pure O25B bioconjugate preparations.

Similarly, host strains for recombinant production of O1A-EPA, O2-EPA, and O6A-EPA were constructed (Table 2). These strains include the rfb clusters related to O1A, O2 and O6A cloned from *E. coli* strain upec032, upec116 and CCUG11309, respectively. Bioconjugates of O1A-EPA, O2-EPA, and O6A-EPA were produced from these recombinant host cells, and purified using methods known in the art in view of the present disclosure.

SDS PAGE quantification was used for purity analysis. Sugar to protein ratios were calculated based on sugar quantification by the anthrone assay (see Laurentin and Edwards, 2003, *Anal Biochem* 315, 143-145) and the BCA assay for protein concentration. Analytical size exclusion chromatography showed a monomeric state of the particles in agreement with the expected hydrodynamic radius of EPA with attached glycan chains.

The bioconjugates and an un-glycosylated EPA reference standard were analyzed by size-exclusion chromatography with multi-angle light scattering (SEC-MALS), in order to quantify the degree of mono- and di-glycosylation of the individual bioconjugates, and to determine the molecular mass (MW) of the protein carrier and of the O-PS attached to it. The samples were separated on a TSKgel-G3000 SWxl column in phosphate buffer (pH 7.0; 50 mM NaCl, 150 mM sodium phosphate) and monitored by UV (214 and 280 nm), refractive index (RI) and multi angle light scattering (MALS).

Vaccine Compositions

This Example illustrates the vaccine compositions useful for the invention.

TABLE 3-1

Vaccine Compositions

| Ingredient | Amount (μg/mL) | |
|---|---|---|
| Active substance | ExPEC4V | Composition 3 |
| O-antigen polysaccharide | | |
| *E. coli* O1A | 8 | 8 |
| *E. coli* O2 | 8 | 8 |
| *E. coli* O6A | 8 | 8 |
| *E. coli* O25B | 8 | 16 |
| Carrier Protein | | |
| EPA | 109 | Expected: 126 |
| Excipients | | |
| TBS buffer, containing | pH 7.4 | |
| Tris | 25 mM | |
| NaCl | 137 mM | |
| KCl | 2.7 mM | |

TABLE 3-2

Vaccine Compositions

| Ingredient | Amount (μg/mL) | |
|---|---|---|
| Active substance | Composition 1 | Composition 2 |
| O-antigen polysaccharide | | |
| *E. coli* O1A | 32 | 16 |
| *E. coli* O2 | 32 | 16 |
| *E. coli* O6A | 32 | 16 |
| *E. coli* O25B | 32 | 32 |
| Carrier Protein | | |
| EPA | Expected: 436 | Expected: 251 |
| Excipients | | |
| TBS buffer, containing | pH 7.4 | |
| Tris | 25 mM | |
| NaCl | 137 mM | |
| KCl | 2.7 mM | |

Each of the above illustrated liquid vaccine compositions is packaged in a vial ready for injection. The vaccine products should be stored at +2° C. to +8° C.

The active substances in the vaccine composition are glycosylated proteins (bioconjugates composed of the EPA protein carrier covalently linked to an *E. coli* O antigen polysaccharide) and the dose is calculated based on the content of the polysaccharide moiety (O antigen) only.

The dose of the EPA carrier protein depends on the polysaccharide-to-protein ratio. The estimated polysaccharide-to-protein ratio was between 15% and 50% depending on the O-antigen serotypes, i.e., the weight of polysaccharide in a conjugate is about 15% to 50% of the weight of the EPA protein carrier in the conjugate. For each serotype in ExPEC4V, the polysaccharide-to-protein ratio was quantified, e.g., the amount of polysaccharide (O-antigen) was measured by the anthrone assay (see Laurentin and Edwards, 2003, *Anal Biochem* 315, 143-145) and the bicinchoninic acid (BCA) assay was used to measure the protein concentration. For each serotype in Products 1-3, the value of EPA provided in Tables 3-1 and 3-2 is the expected value based on the analytical results from ExPEC4V.

Stability of the tetravalent vaccine compositions (O25B, O1A, O2 and O6 bioconjugates) was tested during over a 3 month period. The studies included accelerated and stress storage conditions to identify degradation pathways. These studies demonstrate that the active substances and the tetravalent vaccine compositions are stable for at least three months, and thus are suitable vaccine compositions with respect to stability.

Repeated Dose Toxicity Study in Rats

A good laboratory practice (GLP) toxicity study with a 14-day recovery period was conducted in Sprague-Dawley rats to assess the toxicity and local tolerance of a vaccine composition following 2 intramuscular (i.m.) injections (in quadriceps femoris muscle) on Days 1 and 14. Reversibility, persistence, and delayed occurrence of any changes were assessed after a 14-day recovery period (i.e., on Day 28). The design of the Phase 1-enabling repeated dose toxicity study in the rat is outlined in Table 4.

A dose of 4 μg per O-antigen polysaccharide (PS) of ExPEC4V (total PS dose of 16 g) was tested in this study. This dose is equivalent to the maximum dose that was evaluated in the Phase 1 clinical study described below. Hence the full human dose as used in Phase 1 was administered in the rat GLP toxicology study. The study was performed with a nonclinical batch which was representative for the batch used in the Phase 1 clinical study.

No mortalities were observed during the study, nor any treatment related clinical signs (including body temperature) or ophthalmological observations. Furthermore there were no toxicologically relevant, adverse effects on body weight, body weight gain, food consumption, or hematology, clinical chemistry, coagulation, and urinalysis parameters. There were no test article-related macroscopic findings or differences in organ weights at the end of the treatment (Day 14) and the recovery period (Day 28).

No adverse test article-related microscopic findings were observed. Non-adverse minimal to mild microscopic findings (interstitial inflammation, degeneration/necrosis of myofiber and mixed inflammatory cell infiltrates) were noted at the injection sites in the quadriceps femoris muscle at the end of the treatment period in both the vehicle and treated group. These findings were therefore considered to be not related to administration of the test article, but a result of the dosing procedure (ie, i.m. injection). At the end of the recovery period, Day 1-injection site muscles had recovered, while at the Day 14-injection site, residual minimal mixed cellular inflammation/infiltrates were seen in the muscle, suggesting ongoing recovery in both vehicle and treated animals. Overall, the vaccine was well tolerated and no adverse treatment-related effects were noted.

Immunogenicity of the vaccine has been confirmed, inducing higher serum immunoglobulin G (IgG) titers towards the 4 O-antigens in the vaccinated group compared with vehicles that received only formulation buffer.

Repeated Dose Toxicity Study in Rabbits

A GLP repeated dose toxicity study with a 3-week recovery period was conducted in NZW rabbits (TOX11163, draft report) to assess the toxicity and local tolerance of ExPEC4V following 3 i.m. injections (Days 0, 14, and 28) given 2 weeks apart. Reversibility, persistence, and delayed occurrence of any changes were assessed on Day 49, after a 3-week treatment-free period following the 3rd injection on

TABLE 4

Design of Repeated Dose Toxicity Study in the Rat

| Group | Dose level | Concentration (μg/mL) | Dose volume (mL)[b] | Main Animals (n)[c] | Recovery Animals (n)[d] |
|---|---|---|---|---|---|
| Vehicle[a] | — | — | 0.5 | 10 M + 10 F | 5 M + 5 F |
| ExPEC4V | 4 μg polysaccharide per O-antigen = total of 16 μg polysaccharide per dose + 48 μg per protein carrier EPA dose | polysaccharide per O-antigen: 8 μg/mL + protein carrier EPA: 96 μg/mL | 0.5 | 10 M + 10 F | 5 M + 5 F |

EPA = ExoProtein A/*Pseudomonas aeruginosa* exotoxin A, detoxified form used as protein carrier; F = female, M = male Note:
Day 1 = start of treatment

[a]The vehicle group was administered the formulation buffer (vehicle control)

[b]Animals received 2 injections of 0.25 mL per dosing occasion (left and right hind leg). Animals were dosed on 2 occasions: Day 1 and Day 14

[c]Main animals were euthanized on Day 17

[d]Recovery animals were euthanized on Day 28, ie 14 days after the second treatment Day 28. The design of the Phase 2-enabling repeated dose toxicity study in the rabbit can be found in Table 5.

TABLE 5

Design of Repeated Dose Toxicity Study in the Rabbit

| Group | Dose level[a] (μg/dose) | Concentration (μg/mL) | Volume injected per dosing | ADM[d] | Dosing days | Number of Animals Terminal[e] | Recovery[e] |
|---|---|---|---|---|---|---|---|
| 1 | — | 0 | 2 × 1 mL | ADM 1, 2 ADM 3, 4 ADM 5, 6 | Day 0, Day 14, Day 28 | 5 M + 5 F | 5 M + 5 F |
| 2 | 32[b] | 32 | 1 mL | ADM 1 ADM 3 ADM 5 | Day 0, Day 14, Day 28 | 5 M + 5 F | 5 M + 5 F |
| 3 | 64[c] | 32 | 2 × 1 mL | ADM 1, 2 ADM 3, 4 ADM 5, 6 | Day 0, Day 14, Day 28 | 5 M + 5 F | 5 M + 5 F |

ADM: administration site; F = female; M = male
Note:
Day 0 = start of treatment; Group 1 received saline (control group)
[a]Total O-antigen polysaccharide (1:1:1:1 ratio for O1A, O2, O6A and O25B serotypes, respectively)
[b]8 μg polysaccharide per serotype + 109 μg total EPA carrier protein
[c]16 μg polysaccharide per serotype + 218 μg total EPA carrier protein
[d]ADM1: left - lower part m. biceps femoris; ADM2: right - lower part m. biceps femoris; ADM3: left - upper part m. biceps femoris; ADM4: right - upper part m. biceps femoris; ADM5: left - m. quadriceps femoris; ADM6: right - m. quadriceps femoris
[e]Terminal animals were euthanized on Day 30 and recovery animals on Day 49

A maximum dose of 16 μg per O-antigen PS of ExPEC4V (total PS dose of 64 μg, together with 218 μg EPA carrier protein) was tested in this study. This dose is 4 times higher than the maximum dose that was tested previously in the Phase 1-enabling GLP toxicity study in the rat and is equivalent to the maximum PS (and EPA) dose that is evaluated in the Phase 2 clinical study described below. Hence the full (maximum) human dose as to be used in Phase 2 was administered in this rabbit GLP toxicology study.

The study was performed with the ExPEC4V (containing 32 μg/mL total PS) that was used in the Phase 1 clinical study described below. This batch is considered representative for the vaccine composition that is used in the Phase 2 clinical study described below (containing 128 μg/mL total PS), as the same drug substances are used for both vaccine compositions.

No mortalities were observed during the study. There were no effects on body temperature, body weight, body weight gain, food consumption, ophthalmology, skin evaluation (Draize scoring), clinical chemistry and C-reactive protein.

Females receiving 64 μg ExPEC4V exhibited non-adverse, minimally decreased hemoglobin levels at the end of the treatment and recovery period, with minimal decreases in total RBC count and hematocrit at the end of the recovery period. Fibrinogen was minimally increased 1 week after the 1st injection and at the end of the treatment period in females, but no changes were observed anymore at the end of the treatment-free (recovery) phase.

Shortly after dosing, dark discoloration of the subcutis was noted in some animals of the ExPEC4V-dosed groups, which correlated with the foci/areas of discoloration that were seen at the sites injected on Day 28 in all groups (including control group) at necropsy (Day 30). No abnormalities were noted at the end of the recovery period. Histopathologically multiple foci of mixed inflammatory cell infiltrates (minimal to slight) were seen mainly at the Day 28 injection sites in ExPEC4V-dosed animals. At the end of the recovery period (Day 49) only 1 female in the high dose group exhibited mixed inflammatory cell infiltrates at the injection sites of Day 28, indicating (ongoing) recovery.

Within the draining medial iliac lymph nodes, production (in germinal centers) and sequestration of lymphoblastic cells was seen within the paracortex and/or medullary cords of ExPEC4V-dosed rabbits at the end of the treatment period, resulting in increased overall cellularity. Furthermore lymph nodes were larger in both sexes which correlated with an increased weight in females. These findings were not seen at the end of the recovery period. An increased number of germinal centers was noted in the spleen of treated males and females at the end of the treatment and recovery period, and was accompanied by an increase in spleen weight in both sexes at the end of the treatment period.

These findings are considered non-adverse and related to the immune response to the vaccine administration.

Immunogenicity of the vaccine was confirmed as serum IgG levels against all 4 O-antigen serotypes as well as EPA were elevated in males and females.

Overall, vaccination of rabbits (3 i.m. injections, 2 weeks apart) with ExPEC4V doses containing up to 64 μg total PS was safe and well tolerated. All treatment-related effects observed are considered to reflect a normal, non-adverse response induced by the vaccine administration.

Functionality of Antibody Responses Induced by Vaccines in Rats

To assess the functional activity of vaccine-induced antibody responses of O25B, O1A, O2 and O6A bioconjugates, sera from rats vaccinated with monovalent or tetravalent vaccines containing O25B, O1A, O2 and O6A EPA bioconjugates, each alone or in combination, were analyzed using opsonophagocytic killing (OPK) assays, which measure in vitro complement- and antibody-dependent phagocytosis and killing of bacteria, e.g., E. coli. The OPK assay measures the ability of serum to facilitate opsonophagocytosis and killing of different E. coli serotypes. In 96-well plates, defined dilutions of the sample sera were incubated, in each well, with bacteria from one of the four vaccine-specific *E. coli* serotypes, a defined amount of HL60 cells, and baby rabbit complement. After incubation, a proportion of the mixture was spotted onto tryptic soy agar (TSA) and the number of bacterial colonies was counted. The ability of the antibodies to bind the bacterial cells and activate deposition of the complement and mediate uptake and killing of the bacteria by HL60 cells was expressed as opsonic titer. The opsonic titer or opsonization index (OI) corresponds to the dilution of the sera killing 50% of the bacterial cells. Opsonic indices for pre- and post-immune sera are provided. At least a 4-fold increase of OI from pre- to post-immune is considered significant.

*E. coli* was pre-opsonized with dilutions of serum from vaccinated rats, incubated with complement and phagocytes (differentiated HL60 cells), and the colony forming units (CFUs) were determined. Subsequently, the maximum % killing and Opsonization Indices (OI serum dilution killing of 50% of *E. coli*) were calculated. *E. coli* selected for OPK testing were OC 24453 (serotype O2), OC 24781 (serotype O6A) and OC 24176 (serotype O25B).

Figure 3A:
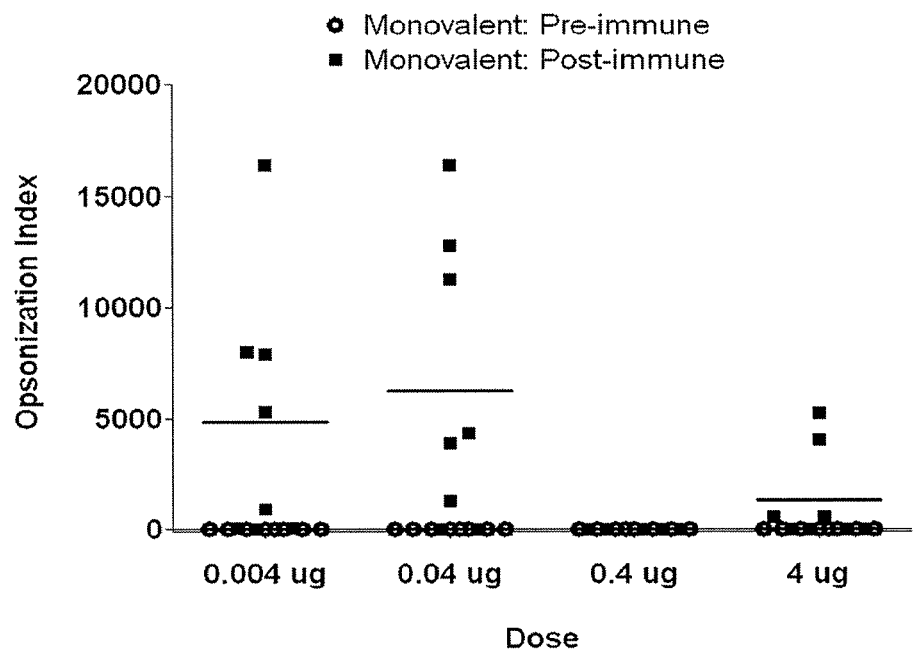
FIGS. 3A-3C depict the opsonization indices (OIs) obtained with sera derived from rats pre-immunization (empty circles) compared to 42 days post-immunization (filled squares) with one priming dose and two booster doses of indicated doses of monovalent vaccine.
Figure 3B:
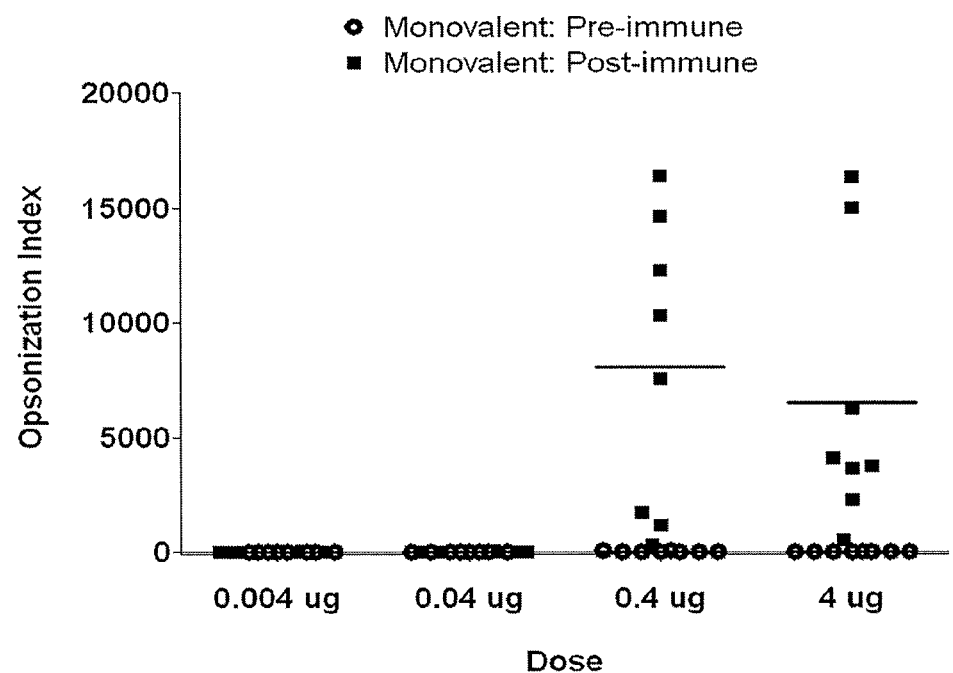
Figure 3C:
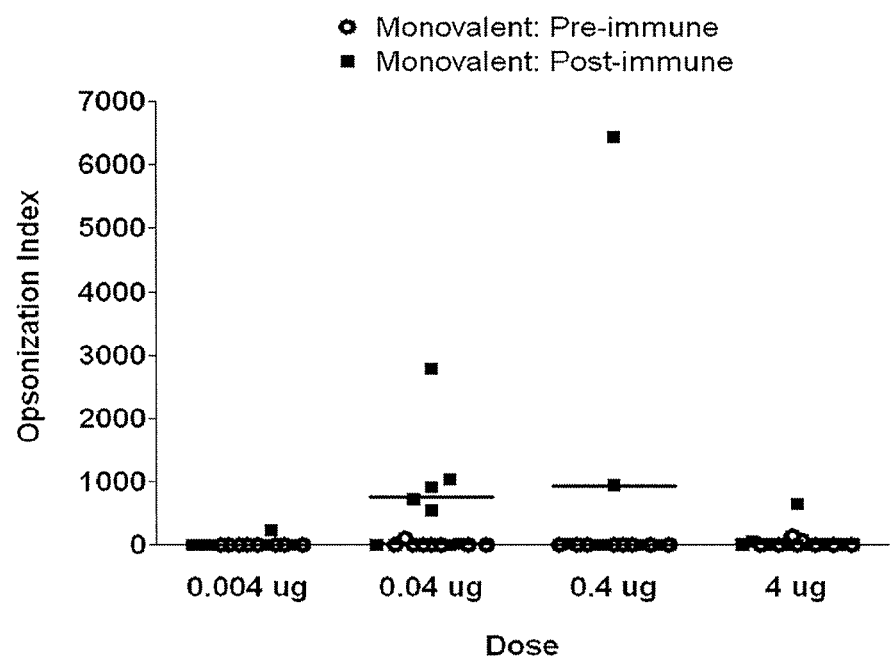

As shown by the results depicted in FIGS. 3A-3C, monovalent vaccines containing O2-EPA, O6A-EPA and O25B-EPA induced robust antibody responses in rats, and such antibody responses are functional in killing *E. coli* from these serotypes.

Table 6 shows the total OI titers for the O-antigens O2, O6A and O25B from rats immunized with the tetravalent vaccine with either 0.4 or 4 μg per O-antigen. The titers were determined in two separate experiments. The 0.4 μg dose induced significant OIs in all animals for the O2 and O6A serotypes. For O25B, 3/8 animals showed a significant increase in OI following immunization with the 0.4 μg dose. Compared to the 0.4 μg dose, the 4 μg dose induced lower OI increases for O2 in all animals. 3/8 animals showed OI increases when the sera from the 4 μg dose group were tested on O25B *E. coli*.

The data confirm that a tetravalent vaccine is able to elicit O-antigen-specific opsonic antibodies against O2, O6A and O25B in animals, demonstrating that the vaccine compositions described herein induce antibody responses against *E. coli* serotypes from which O-antigens are included in the vaccine, and that such antibody responses are functional in killing *E. coli* from these serotypes.

TABLE 6

OIs against *E. coli* O2, O6A and O25B. OIs for individual pre-vaccination and post 3 vaccination sera from two separate experiments are shown for all animals.

Tetravalent-EPA Rat Serum Opsonization Indices (OI)

| | O2 *E. coli* | | | | O6 *E. coli* | | | | O25 *E. coli* | | | |
| | 0.4 ug Dose | | 4 ug Dose | | 0.4 ug Dose | | 4 ug Dose | | 0.4 ug Dose | | 4 ug Dose | |
| Animal No. | Exp. 1 | Exp. 2 | Exp. 1 | Exp. 2 | Exp. 1 | Exp. 2 | Exp. 1 | Exp. 2 | Exp. 1 | Exp. 2 | Exp. 1 | Exp. 2 |
|---|---|---|---|---|---|---|---|---|---|---|---|---|
| 1: Pre-vacc | 6 | 7 | 5 | 0 | 17 | 6 | 6 | 16 | 2'404 | 2'082 | 0 | 0 |
| Post vacc | >16384 | 1'476 | 293 | 32 | 202 | 226 | 2'045 | 2'821 | 1'847 | 1'578 | 9 | 0 |
| 2: Pre-vacc | 21 | 11 | 11 | 20 | 11 | 90 | 0 | 0 | 0 | 0 | 0 | 0 |
| Post vacc | 11'148 | >16384 | 150 | 120 | 436 | 475 | 10'262 | 11'460 | 0 | 0 | 4 | 0 |
| 3: Pre-vacc | 6 | 6 | 0 | 0 | 0 | 5 | 0 | 0 | 0 | 0 | 0 | 0 |
| Post vacc | 11'073 | >16384 | 46 | 19 | 98 | 37 | 7'959 | 8'597 | 6 | 0 | 355 | 197 |
| 4: Pre-vacc | 5 | 5 | 5 | 6 | 23 | 17 | 0 | 0 | 0 | 0 | 0 | 0 |
| Post vacc | >16384 | 63 | 57 | 45 | 108 | 116 | 2'189 | 4'488 | 0 | 0 | 70 | 26 |
| 5: Pre-vacc | 7 | 0 | 0 | 4 | 30 | 8 | 8 | 7 | 0 | 0 | 0 | 0 |
| Post vacc | 10'413 | 7'050 | 105 | 108 | >16,384 | 12'672 | 3'107 | 7'564 | 0 | 0 | 105 | 69 |
| 6: Pre-vacc | 8 | 0 | 8 | 7 | 299 | 164 | 5 | 0 | 269 | 154 | 0 | 0 |
| Post vacc | 89 | 34 | 24 | 17 | 1'725 | 1'475 | 540 | 896 | 0 | 0 | 0 | 0 |
| 7: Pre-vacc | 9 | 9 | 6 | 6 | 18 | 21 | 22 | 5 | 0 | 0 | 0 | 0 |
| Post vacc | >16384 | >16384 | 109 | 92 | 1'249 | 1'863 | 160 | 143 | 1'130 | 630 | 9 | 8 |
| 8: Pre-vacc | 4 | 6 | 6 | 5 | 26 | 22 | 0 | 0 | 0 | 0 | 0 | 0 |
| Post vacc | 5'058 | 4'201 | 39 | 25 | 6'590 | 3'826 | 288 | 656 | 3'336 | 1'986 | 0 | 0 |
| Pre-vacc Av | 8 | 5 | 5 | 6 | 53 | 42 | 5 | 3 | 334 | 280 | 0 | 0 |
| Post-vacc Av | 10'867 | 7'747 | 103 | 57 | 3'349 | 2'586 | 3'319 | 4'578 | 790 | 524 | 69 | 37 |

Effects in Human—Phase I Study

ExPEC4V has been tested in a first-in-human Phase 1 study, which enrolled a total of 194 subjects. This Phase 1 study is a randomized, placebo-controlled, multicenter study. The study was conducted in a single-blind manner as the investigator and study staff knew the randomization group of the subjects while the subjects were required to be blinded to their randomization group at all times.

The objective of this first-in-human study was to evaluate the safety, immunogenicity, and efficacy of the candidate vaccine in healthy women aged ≥18 to ≤70 years with a history of recurrent urinary tract infection (rUTI). The primary objective of the study was the comparison of solicited and unsolicited adverse events (AEs) and serious adverse events (SAEs) between subjects who received ExPEC4V and subjects who received placebo. The main secondary objectives included immunogenicity parameters, the number of symptomatic UTI episodes caused by *E. coli* vaccine-serotypes, and the rate of occurrence and clinical symptoms of vaccine-serotype-specific *E. coli* UTI.

Eligible subjects were required to have at least 3 independent UTI episodes in the last 12 months or at least 2 independent UTI episodes in the previous 6 months; at least 1 of the independent UTI episodes had to be due to a culture-confirmed *E. coli* infection. A total of 194 subjects were enrolled and randomized to a single i.m. dose of 0.5 mL of ExPEC4V or placebo (see Table 7). The enrollment was done in a staggered approach to assess Day 14 safety data before proceeding to the next phase:

1. The first 8 subjects were randomized (3:1) to a dose of 1 μg of each PS, or placebo
2. The following 8 subjects were randomized (3:1) to a dose of 4 μg of each PS, or placebo 3. The remaining 178 subjects were randomized (1:1) to a dose of 4 μg of each PS, or placebo.

TABLE 7 the demographic and baseline characteristics of the subjects enrolled in the Phase 1 study.

|  | Placebo<br>N = 95 | ExPEC4V | | Total<br>N = 194 |
|---|---|---|---|---|
|  | | 1 μg polysaccharide<br>per serotype[a]<br>N = 6 | 4 μg polysaccharide<br>per serotype[b]<br>N = 93 | |
| Age (years) | | | | |
| N | 95 | 6 | 93 | 194 |
| Mean (SD) | 42.1 (15.9) | 28.1 (9.6) | 42.0 (17.6) | 41.6 (16.7) |
| Median (range) | 42.6 (18, 71) | 23.1 (20, 43) | 38.5 (19, 72) | 39.6 (18, 72) |
| Race | | | | |
| N | 95 | 6 | 93 | 194 |
| Caucasian | 91 (96%) | 6 (100%) | 87 (94%) | 184 (95%) |
| Other | 4 (4%) | 0 | 6 (6%) | 10 (5%) |
| Weight (kg) | | | | |
| N | 95 | 6 | 93 | 194 |
| Mean (SD) | 63.1 (11.0) | 59.7 (10.3) | 63.8 (11.0) | 63.3 (10.9) |
| Median (range) | 61 (46.2, 95.0) | 56.5 (50, 79) | 63 (44, 105) | 61 (44, 105) |
| Body Mass Index (kg/m$^2$) | | | | |
| N | 95 | 6 | 93 | 194 |
| Mean (SD) | 23.2 (4.1) | 21.1 (4.3) | 23.3 (3.8) | 23.2 (3.9) |
| Median (range) | 22 (17.8, 33.7) | 19.9 (17.5, 29.4) | 22.7 (17.6, 34.3) | 22.2 (17.5, 34.3) |
| Menopausal Status | | | | |
| N | 95 | 6 | 93 | 194 |
| Premenopausal | 64 (67%) | 6 (100%) | 57 (61%) | 127 (65%) |
| Child Bearing Potential | | | | |
| N | 64 | 6 | 57 | 127 |
| Yes | 55 (86%) | 6 (100%) | 54 (95%) | 115 (91%) |

[a]The ExPEC4V doses contain O-antigen polysaccharides of the 4 ExPEC serotypes O1A, O2, O6A, and O25B.

At first visit, eligible subjects that have provided informed consent were screened and compliance for inclusion/exclusion criteria was confirmed. Blood was drawn and urine was collected. At visit 2 (day 1), each subject received one intramuscular injection of 0.5 ml of solution (ExPEC4V or placebo) in the deltoid muscle. The reduced dose of the candidate vaccine contained 1 μg of each polysaccharide (total 4 μg polysaccharide). The target dose of the candidate vaccine contained 4 μg of each polysaccharide (total 16 μg polysaccharide).

Safety was evaluated based on solicited local (pain, erythema, and swelling at the injection site) and systemic (fever, i.e., body temperature ≥38° C.) AEs collected in a diary from Day 1 postvaccination until Day 7 and on AEs and SAEs collected until Day 270 (end of study visit). Immunogenicity was evaluated by qualified enzyme-linked immunosorbent assays (ELISA) and opsonophagocytic killing (OPK) assays using serum from blood samples taken prevaccination on Day 1 and postvaccination on Days 30 and 270.

Descriptive statistics (n, mean, standard deviation, median and ranges for continuous variables, frequencies and percentages for categorical variables) are provided by treatment group and/or visit, where applicable. All data are listed by subject, treatment group and, where applicable, visit. All subjects from Group B receiving placebo are combined to form the placebo treatment group.

Safety

To date, none of the following has been identified from the Phase 1 study (which is still on-going): adverse drug reactions, significant clinical laboratory abnormality, cardiovascular, pulmonary, central nerve system, renal, or other significant adverse effects, overdose. Occurrence of adverse events and severe adverse events were comparable between the placebo and vaccinated groups.

Immunogenicity—Total Antibody Titer

To assess the immunogenicity of the vaccine components, sera from women participating in the clinical study were obtained and analyzed by ELISA to quantify IgG against the four different O-antigens included in the tetravalent vaccine (*E. coli* O1, *E. coli* O2, *E. coli* O6, and *E. coli* O25B). Total Day 1 (prevaccination) and Day 30 serum IgG antibody titers were assessed by a qualified ELISA optimized for each serotype isolate using purified serotype-specific O-antigen as primary assay antigen. Total IgG antibody titers per serotype were calculated using a 4-parameter logistic curve fit to determine per sample half maximal effective concentration ($EC_{50}$) values.

1 μg Polysaccharide Per Serotype in ExPEC4V (N=6)

Six subjects received an ExPEC4V dose of 1 μg PS per serotype (4 μg total PS). Analysis of serotype-specific immune responses of these subjects by Day 30 showed the proportion of subjects with a ≥2-fold increase in total antibodies per serotype was 50% (serotype O1A), 83% (serotype O2), 50% (serotype O6A), and 67% (serotype O25B). The proportion of subjects with a ≥4-fold increase in antibody titers was lower, i.e., 17% (serotype O6A), 33% (serotype 1A), 33% (serotype 2) and 50% (serotype O25B).

Analysis of responses of the 1 μg PS per serotype dose group yielded similar magnitude increases across the 4 serotypes. For serotypes O1A, O2, O6A, and O25B comparing Day 30 to Day 1, median fold increases in antibody titers were 2.5, 3.7, 2.2, and 4.1, respectively. Individual subject fold increases ranged from 1 to 6 for serotypes O1A and O2, from 1 to 7 for serotype O6A, and from 1 to 11 for serotype O25B. Geometric mean titer (GMT) values on Day 30 were 4,053, 13,768, 1,236, and 227 for the respective 4 serotypes (Table 8), representing approximately a 2.2-3.5 fold increase over Day 1 GMT values.

These data indicate an overall increase in the antibody titers associated with the higher 4 μg PS per serotype dose compared to the 1 μg PS per serotype dose. Although these results suggest greater variability associated with the titers of the higher dose group compared to the lower dose group, the small number of subjects in the 1 μg per subject dose limit the interpretation of any observed differences. Differ-

TABLE 8

GMT and 95% Confidence Intervals in ELISA-Determined Total Antibody Titers from Day 1 (Prevaccination) to Day 30 - Phase 1 Study

| Antibody | | Placebo N = 95 | | ExPEC4V | | | |
|---|---|---|---|---|---|---|---|
| | | | | 1 μg polysaccharide per serotype$^a$ N = 6 | | 4 μg polysaccharide per serotype$^b$ N = 93 | |
| | | Day 1 | Day 30 | Day 1 | Day 30 | Day 1 | Day 30 |
| O1A | GMT | 1,895 | 1,887 | 1,720 | 4,053 | 1,807 | 9,460 |
| | 95% CI | 1,515-2,369 | 1,517-2,347 | 633-4,672 | 2,160-7,605 | 1,489-2,191 | 7,511-11,916 |
| O2 | GMT | 3,529 | 3,502 | 4,266 | 13,768 | 2,855 | 27,973 |
| | 95% CI | 2,926-4,257 | 2,910-4,214 | 1,731-10,511 | 6,516-29,091 | 2,279-3,576 | 22,026-35,526 |
| O6A | GMT | 943 | 953 | 558 | 1,236 | 920 | 4,475 |
| | 95% CI | 777-1,145 | 789-1,151 | 292-1,067 | 799-1,911 | 743-1,138 | 3,508-5,549 |
| O25B | GMT | 285 | 282 | 64 | 227 | 261 | 2,164 |
| | 95% CI | 211-384 | 209-381 | 16-254 | 53-976 | 188-363 | 1,676-2,794 |

Figure 4:
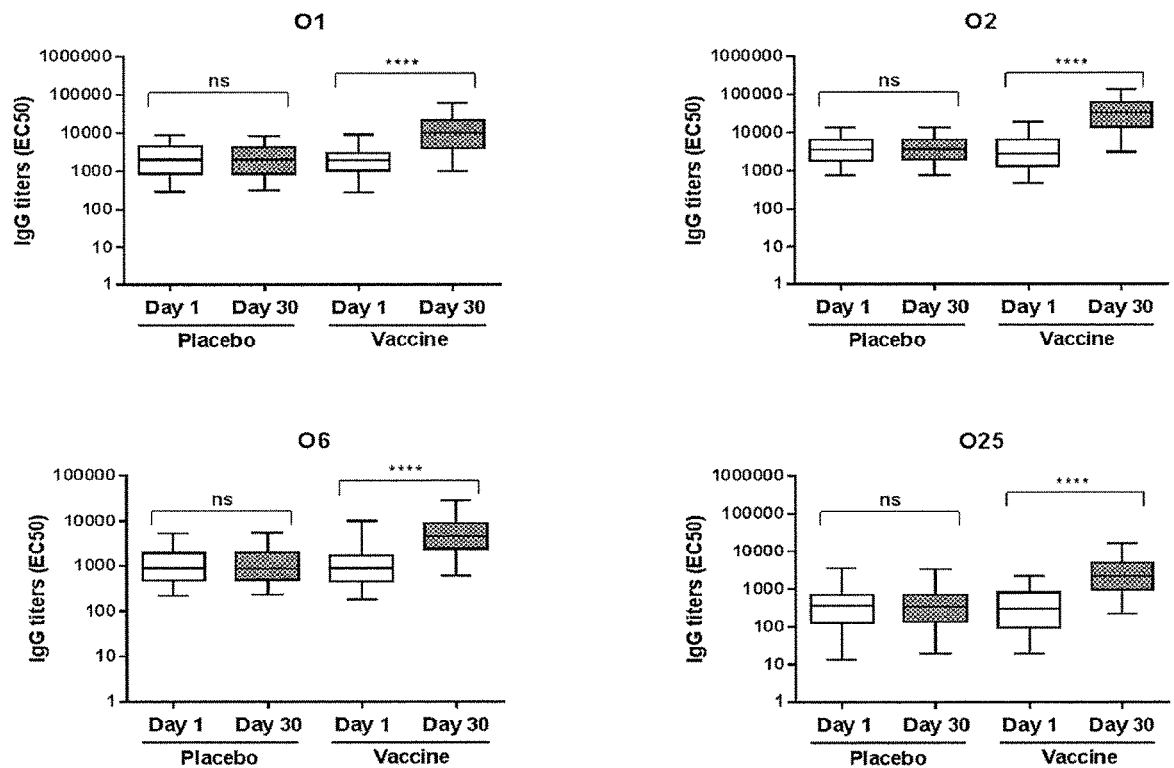
FIG. 4 shows the ELISA titers obtained with sera from human subjects vaccinated with a placebo or a tetravalent vaccine comprising E. coli antigens O1A, O2, O6A and O25B at 4 µg polysaccharide per serotype; a significant increase in the ELISA titers between post- (30 days after injection) and pre-injection (day 1) was observed only in the vaccinated groups (* represents statistical significance, wherein multiple * represent increased degree of significance; ns, no significant difference)
Figure 5A:
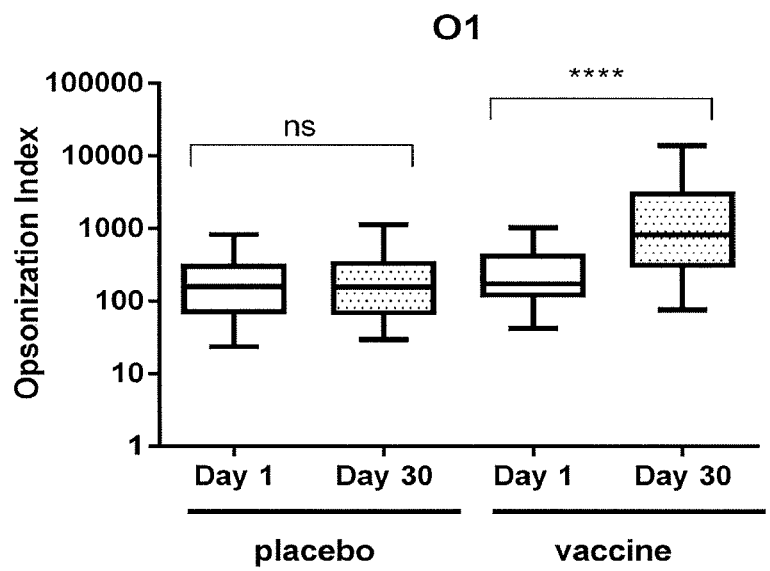
FIGS. 5A-5D depict the OIs obtained with sera derived from human subjects vaccinated with a tetravalent vaccine comprising E. coli antigens O1A, O2, O6A and O25B at 4 µg polysaccharide per serotype; immune response as indicated by OI against placebo and components of the tetravalent vaccine.
Figure 5B:
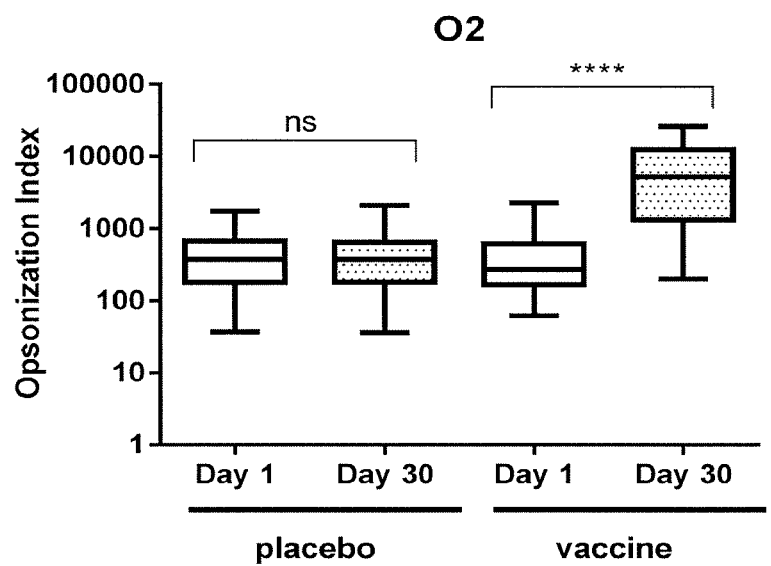
Figure 5C:
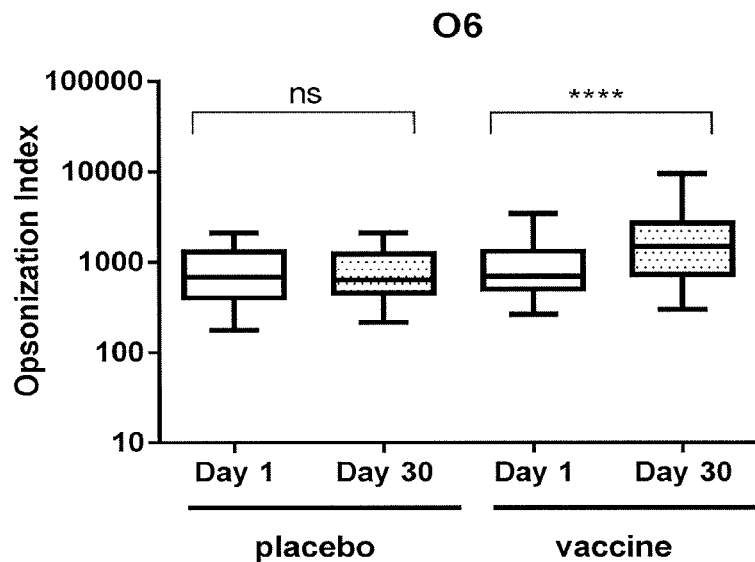
Figure 5D:
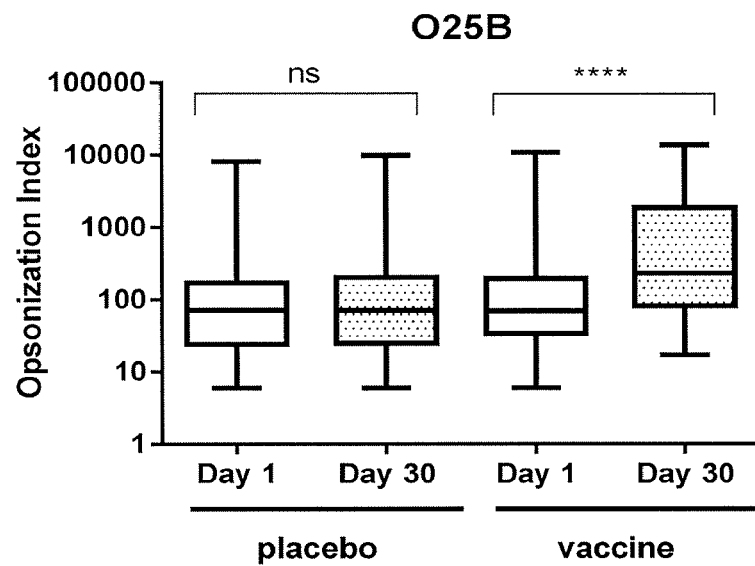

In comparison to the dose containing 1 μg PS per serotype (4 μg total PS), administration of an ExPEC4V dose of 4 μg PS per serotype (16 μg total PS) yielded a more robust immune response. Analysis of these subjects by Day 30 showed the proportion of subjects with a ≥2-fold increase in total antibodies per serotype was 81% (serotype O1A), 92% (serotype O2), 80% (serotype O6A), and 82% (serotype O25B). The proportion of subjects with a ≥4-fold increase in antibody titers ranged from 57% (serotypes O1A and O6A) to 80% (serotype O2), which is lower than the proportion with a 2-fold increase, but notably higher than observed with the dose containing 1 μg PS per serotype. See also FIG. 4, a robust immune response to each of O1A, O2, O6A, and O25B was observed, and that a significant increase in the ELISA titers between post (30 days after injection) and pre-injection (day 1) was observed only in the vaccinated groups (V_Day 30 v.s. V_Day 1), but not in the placebo groups (P_Day 30 v.s. P_Day 1).

Analysis of responses of the 4 μg PS per serotype group yielded median fold increases that were larger than those of the 1 μg PS per serotype dose group. For serotypes O1A, O2, O6A, and O25B comparing Day 30 to Day 1, $EC_{50}$ median fold increases were 4.6, 9.4, 4.9, and 5.9, respectively. The magnitude and variability in the fold increases were greater with this dose group, ranging from 1 to 96 for serotype O1A, from 1 to 165 for serotype O2, from 0 to 61 for serotype O6A, and from 1 to 579 for serotype O25B. GMT values on Day 30 were 9,460, 27,973, 4,475, and 2,164 for the respective 4 serotypes (Table 8), representing approximately a 4.9 to 9.8 fold increase over Day 1 GMT values.

Conclusion

These interim results show a vaccine-specific immune response in healthy subjects administered the 1 μg PS per serotype ExPEC4V dose, and a comparatively greater increase in the immune response with the higher 4 μg PS per serotype ExPEC4V dose, over a 30-day observational period. The lack of relevant change in antibody titers of the 95 subjects in the placebo group over this period suggests the antibody response in ExPEC4V recipients is vaccine-mediated, and is not due to environmental exposure to ExPEC bacteria.

ences were also observed within each dose group in the relative IgG titers per serotype, with the titer for antibodies to the O25B antigen being the lowest (Table 8).

Functional Antibody Response

OPK assays were used to assess the functional antibody response of women participating in the clinical study. Sera were collected from study participants. *E. coli* was pre-opsonized with dilutions of serum from the vaccinated women, incubated with complement and phagocytes (differentiated HL60 cells), and the remaining colony forming units (CFUs) was determined. Subsequently, the maximum percent killing and Opsonization Indices (OI: serum dilution killing of 50% of *E. coli*) were calculated. *E. coli* selected for OPK testing were OC 24452 (serotype O1A), OC 24453 (serotype O2), OC 24454 (serotype O6A), and OC 24176 (serotype O25B).

Day 1 and Day 30 sera were assessed for functional antibodies (measured as the opsonization index [OI], or serum concentration yielding a 50% decrease in *E. coli* colony forming units) by an OPK assay, optimized using selected serotype O1A, O2, O6A, or O25B ExPEC strains, with human complement and HL60 phagocytic cells. Functional antibody titers for serotype O25B are included in the interim analysis based on preliminary assessments of titer accuracy and reproducibility. For all serotypes, functional antibody titers are determined from measurements of *E. coli* opsonophagocytic-mediated killing using the NICE program, developed by the U.S. National Institute of Standards and Technology, and the Opsititer3 program, developed and licensed from the University of Alabama. For the interim analysis, OPK titers were determined for the 194 subjects, including 95 subjects receiving placebo, 6 subjects receiving the ExPEC4V 1 μg PS (per serotype) vaccine and 93 subjects receiving the ExPEC4V 4 μg PS (per serotype) vaccine.

Placebo Recipients (N=95)

As observed with ELISA testing, placebo recipients (95 subjects) showed similar OPK responses for Day 1 and Day 30 sera vs ExPEC4V serotypes, with little or no observed change to most respective per-subject OPK titer values.

These results indicate a stable functional antibody titer for most or all placebo subjects over this time period.

1 μg Polysaccharide Per Serotype ExPEC4V (N=6)

Six subjects received an ExPEC4V dose of 1 μg PS per serotype (4 μg total PS). Analysis of serotype-specific immune responses of these subjects by Day 30 showed the proportion of subjects with a ≥2-fold increase in total antibodies per serotype was 33% (serotype O1A), 67% (serotype O2), and 0% (serotypes O6A and O25B). For serotypes O1A and O2, the proportion of subjects with a ≥4-fold increase in antibody titers decreased to 17% and 50%, respectively.

For serotypes O1A, O2, O6A, and O25B comparing Day 30 to Day 1, median fold increases in antibody titers were 1.0, 4.8, 0.9, and 1.0, respectively. Individual subject fold increases ranged from 0.6 to 8.1 for serotype O1, from 0.3 to 9.5 for O2, from 0.8 to 1.3 for serotype O6A, and from 0.5 to 1.5 for serotype O25B. Geometric mean titer (GMT) values on Day 30 were 429, 1834, 1,136, and 51 for the respective 4 serotypes, representing approximately a 1.0-2.8 fold increase over Day 1 GMT values.

4 μg Polysaccharide Per Serotype ExPEC4V (N=93)

Administration of an ExPEC4V dose of 4 μg PS per serotype (16 μg total PS) yielded a functional immune response for all ExPEC 4V serotypes. Analysis of these subjects by Day 30 showed the proportion of subjects with a ≥2-fold increase in OI values per serotype was 63% (serotype O1A), 90% (serotype O2), 33% (serotype O6A), and 55% (serotype O25B). The proportion of subjects with a ≥4-fold increase in OI values ranged from 20% (serotype O6A) to 82% (serotype O2); as expected, these proportions were consistently lower than those observed for the ≥2-fold increase.

For serotypes O1A, O2, O6A, and O25B comparing Day 30 to Day 1, OI median fold OPK titer increases were 3.5, 14.7, 1.4, and 2.5, respectively. The magnitude of the per subject fold increases with this dose group ranged from 0.5 to >292 for serotypes O1A and O2, from 0.3 to 26.4 for serotype O6A, and from 0.1 to 272.8 for serotype O25B. As depicted in FIGS. 5A-5D, a robust functional immune response to each of O1A, O2, O6A, and O25B was observed, and a significant increase in the OI between post- and pre-injection was observed only in the vaccinated groups, not the placebo groups.

GMT values on Day 30 were 950.5, 4,132, 1,542, and 414.7 for the respective 4 serotypes (Table 9), representing approximately a 2- to 14-fold increase over Day 1 GMT values. These data indicate an overall increase in the Day 30 functional antibody titers associated with the 4 μg PS per serotype dose, across all ExPEC 4V serotypes.

TABLE 9

GMT and 95% Confidence Intervals in OPK-Determined Functional Antibody Titers from Day 1 (Prevaccination) to Day 30 - Phase 1 Study

| | | Opsonization Index[a] | | | | | |
|---|---|---|---|---|---|---|---|
| | | Placebo N = 95 | | 1 μg polysaccharide per serotype[b] N = 6 | | 4 μg polysaccharide per serotype[b] N = 93 | |
| Antibody | | Day 1 | Day 30 | Day 1 | Day 30 | Day 1 | Day 30 |
| O1A | GMT | 156 | 161 | 288 | 429 | 192.5 | 950.5 |
| | 95% CI | 126.4-192.5 | 131-197.8 | 94-881 | 203-910 | 158.9-233.3 | 692.8-1,304.1 |
| O2 | GMT | 341.9 | 341.6 | 652 | 1834 | 301.3 | 4,132 |
| | 95% CI | 275.2-424.8 | 273.8-426.3 | 214-1980 | 425-7913 | 237.6-382.2 | 3,034.9-5,625. |
| O6A | GMT | 692.6 | 715.1 | 1147 | 1136 | 790.6 | 1,542 |
| | 95% CI | 589.4-813.8 | 614.5-832.2 | 794-1657 | 749-1721 | 676.7-923.7 | 1,263.7-1,881. |
| O25B | GMT | 86.6 | 97.3 | 52 | 51 | 114 | 414.7 |
| | 95% CI | 58.4-128.5 | 64.3-147.2 | 27-103 | 28-92 | 74.6-174.5 | 273.5-629 |

Conclusion

These interim results show a vaccine-specific functional immune response in healthy subjects administered the 4 μg PS per serotype ExPEC4V dose, over a 30-day observational period. The lack of significant change in antibody titers of the 95 subjects in the placebo group over this period (FIGS. 5A-5D and Table 9) is consistent with ELISA results and supports the conclusion that an antibody response to vaccination has been demonstrated across the 4 ExPEC serotypes.

Interim immunogenicity results from the Phase 1 study show for both total (ELISA) and functional (OPK) antibody titers a vaccine-specific immune response in healthy subjects administered the 1 μg PS per serotype ExPEC4V dose, and a comparatively greater increase in the immune response with the higher 4 μg PS per serotype ExPEC4V dose, over a 30-day observational period. Comparison with serotype-specific fold increases observed with ELISA testing, the OPK assay showed similar response levels for serotypes O1A and O2 for both assays, but somewhat lower levels of OPK % subject responses with serotypes O6A and O25B. The selective decrease in OPK response of some subjects for serotypes O6A and O25B is under investigation.

Notably, the GMT value in OPK-determined functional antibody titer for O25B antigen is lower than those for the other antigens (O1A, O2 and O6A). The OPK assay has been accepted as a better surrogate assay for immune protection induced by the PS conjugate vaccine against *Streptococcus pneumoniae* (Prevenar©), since the ELISA may not differentiate nonprotective low-avidity antibodies from protective high-avidity antibodies (Kim et al., *Clin Diagn Lab Immunol.* 2003 10(4):616-21)

Effects in Human—Phase II Study

Based on the interim results from the Phase I study, a Phase II study will be conducted. This randomized, double-blind, placebo-controlled multicenter study is planned to evaluate safety, tolerability, and immunogenicity of 5 different doses in men and women in stable health, stratified by age: ≥18 to <50 years old (N=275) and ≥50 years old (N=560).

Two vaccine compositions, i.e., Products 1 & 2 provided in Table 3-2, having two different polysaccharide concentrations using the same active substances as those used in ExPEC4V will be used in the Phase II study. More specifically, the Composition 1 formulation contains 32, 32, 32, 32 µg/ml per O-antigen polysaccharide (PS) of the E. coli serotypes O1A, O2, O6A and O25B, respectively, without adjuvant. The Composition 2 formulation contains 16, 16, 16, 32 µg/ml per O-antigen PS of the E. coli serotypes O1A, O2, O6A and O25B, respectively, without adjuvant.

Different dosages and ratios of the active substances will be tested in the phase II study. More specifically, the enrolled subjects will be randomized and divided into six arms: (i-v) five different doses of candidate vaccine and (vi) placebo. Each subject will receive a single i.m. dose of Composition 1, Composition 2 or placebo. The target dose for the E. coli O-antigens O1A:O2:O6A:O25B per injection of Composition 1 or 2 is: 4:4:4:4 µg (i.e., the same as the highest dose used in the phase study above), 4:4:4:8, 8:8:8:8, 8:8:8:16 and 16:16:16:16 µg. The objective of the study is to assess the safety, immunogenicity, and efficacy of the 5 different doses of the tetravalent E. coli bioconjugate vaccine.

Sequences

| Description | SEQUENCE | SEQ ID NO. |
|---|---|---|
| Detoxified EPA protein comprising 4 optimized N-glycosylation sequences | GSGGGDQNATGSGGGKLAEEAFDLWNECAKACVLD LKDGVRSSRMSVDPAIADTNGQGVLHYSMVLEGGN DALKLAIDNALSITSDGLTIRLEGGVEPNKPVRYS YTRQARGSWSLNWLPIGHEKPSNIKVFIHELNAGN QLSHMSPIYTIEMGDELLAKLARDATFFVRAHESN EMQPTLAISHAGVSVVMAQAQPRREKRWSEWASGK VLCLLDPLDGVYNYLAQQRCNLDDTWEGKIYRVLA GNPAKHDLDIKDNNNSTPTVISHRLFPEGGSLAAL TAHQACHLPLEAFTRHRQPRGWEQLEQCGYPVQRL VALYLAARLSWNQVDQVIRNALASPGSGGDLGEAI REQPEQARLALTLAAAESERFVRQGTGNDEAGAAS ADVVSLTCPVAKDQNRTKGECAGPADSGDALLERN YPTGAEFLGDGGVSFSTRGTQNWTVERLLQAHRQL EERGYVFVGYHGTFLEAAQSIVFGGVRARSQDLDA IWRGFYIAGDPALAYGYAQDQPEDARGRIRNGALL RVYVPRWSLPGFYRTGLTLAAPEAAGEVERLIGHP LPLRLDAITGPEEEGGRVTILGWPLAERTVVIPSA IPTDPRNGVVDLDPSSIPDKEQAISALPDYASQPG KPPREDLKLGSGGGDQNAT | 1 |
| N-glycosylation consensus sequence | Asn-X-Ser(Thr), wherein X can be any amino acid except Pro | 2 |
| N-glycosylation consensus sequence | Asp(Glu)-X-Asn-Z-Ser(Thr), wherein X and Z are independently selected from any natural amino acid except Pro | 3 |

The embodiments described herein are intended to be merely exemplary, and those skilled in the art will recognize, or be able to ascertain using no more than routine experimentation, numerous equivalents to the specific procedures described herein. All such equivalents are considered to be within the scope of the present invention and are covered by the following claims.

All references (including patent applications, patents, and publications) cited herein are incorporated herein by reference in their entirety and for all purposes to the same extent as if each individual publication or patent or patent application was specifically and individually indicated to be incorporated by reference in its entirety for all purposes.

REFERENCES (1) Johnson et al., J Lab Clin Med. 2002; 139(3):155-162
(2) Kohler et al., Int J Med Microbiol. 2011; 301(8):642-647
(3) Foxman, Am J Med. 2002; 113 Suppl 1A:5S-13S;
(4) Russo et al., Microbes Infect. 2003; 5(5):449-456
(5) Schito et al., 2009, Int. J. Antimicrob. Agents 34(5):407-413
(6) Pitout et al., 2012, Expert Rev. Anti. Infect. Ther. 10(10): 1165-1176
(7) Johnson et al., Antimicrob Agents Chemother. 2010; 54(1):546-550
(8) Rogers et al., J Antimicrob Chemother. 2011; 66(1):1-14
(9) Banerjee et al., Antimicrob Agents Chemother. 2014; 58(9):4997-5004
(10) Stenutz et al., FEMS Microbial Rev. 2006; 30: 382-403
(11) Russo et al., Vaccine. 2007; 25: 3859-3870
(12) Lipsitch, Emerging Infectious Diseases; 1999,5:336-345
(13) WO 2006/119987
(14) WO 2009/104074
(15) International Patent Application No. PCT/EP2015/053739 (published as WO 2015/124769)
(16) Ihssen et al., 2010, Microbial Cell Factories 9, 61
(17) Lukac et al., Infect Immun, 56: 3095-3098, 1988
(18) Ho et al., Hum Vaccin, 2:89-98, 2006
(19) Pawlowski et al., 2000, Vaccine 18:1873-1885
(20) Robbins et al., 2009, Proc Natl Acad Sci USA 106: 7974-7978
(21) Saraswat et al., 2013, Biomed. Res. Int. ID #312709 (p. 1-18)
(22) WO/2009/104074
(23) Datsenko and Wanner (2000) Proc Natl Acad Sci USA 97: 6640-6645
(24) WO 2014/057109

What is claimed is:

1. A composition comprising an *E. coli* O25B antigen polysaccharide at a first concentration, and *E. coli* O1A, O2 and O6A antigen polysaccharides each at a concentration that is independently 40% or 50% of the first concentration, each of the *E. coli* O25B, O1A, O2 and O6A antigen polysaccharides are independently covalently bound to a detoxified exotoxin A of *Pseudomonas aeruginosa* (EPA) carrier protein, and the first concentration is 8 to 48 μg/ml.

2. The composition of claim 1, wherein each of the *E. coli* O1A, O2 and O6A antigen polysaccharides have the same concentration.

3. The composition of claim 1, wherein each of the *E. coli* O1A, O2 and O6A antigen polysaccharides have different concentrations.

4. The composition of claim 1, comprising 16 μg/ml of the O25B antigen polysaccharide.

5. The composition of claim 1, comprising 32 μg/ml of the O25B antigen polysaccharide.

6. A multivalent immune composition comprising an *E. coli* O25B antigen polysaccharide at a first dose of 5 to 18 μg, and an *E. coli* O1A antigen polysaccharide, an *E. coli* O2 antigen polysaccharide and an *E. coli* O6A antigen polysaccharide each at a dose that is independently 40% or 50% of the first dose, wherein each of the *E. coli* O25B, O1A, O2 and O6A antigen polysaccharides are independently covalently bound to a detoxified exotoxin A of *Pseudomonas aeruginosa* (EPA) carrier protein.

7. The multivalent immune composition of claim 6, wherein the *E. coli* O25B antigen polysaccharide comprises the structure of Formula O25B':

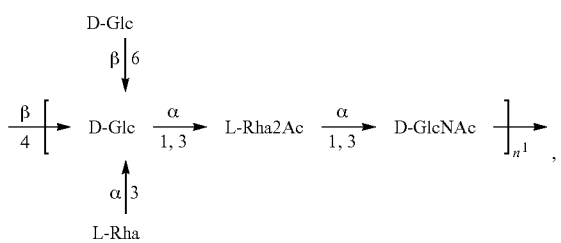

the *E. coli* O1A antigen polysaccharide comprises the structure of Formula O1A':

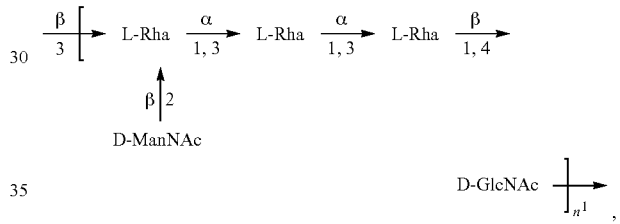

the *E. coli* O2 antigen polysaccharide comprises the structure of Formula O2':

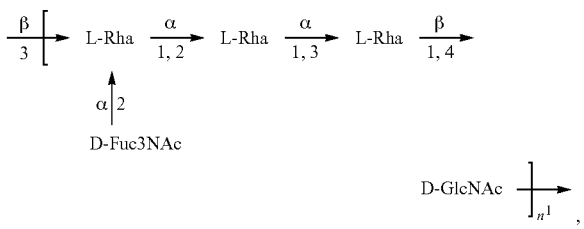

and
the *E. coli* O6A antigen polysaccharide comprises the structure of Formula O6A':

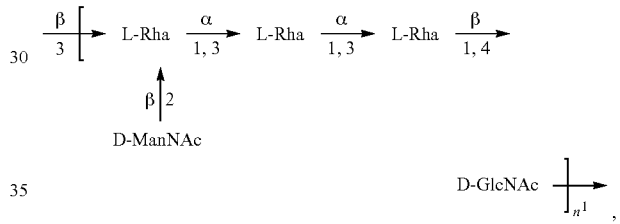

wherein n is independently an integer of 5 to 25, and each of the *E. coli* O25B, O1A, O2 and O6A antigen polysaccharides are independently covalently bound to a carrier protein having the amino acid sequence of SEQ ID NO:1.

8. A method of inducing an immune response to extra-intestinal pathogenic *E. coli* (ExPEC) in a subject, comprising administering to the subject a composition of claim 1.

9. The method of claim 8, wherein the subject is a human.

10. A method of inducing an immune response to extra-intestinal pathogenic *E. coli* (ExPEC) in a subject, comprising administering to the subject a first effective amount of an *E. coli* O25B antigen polysaccharide, and a second effective amount of each of an *E. coli* O1A antigen polysaccharide, an *E. coli* O2 antigen polysaccharide and an *E. coli* O6A antigen polysaccharide, each of the *E. coli* O1A, O2 and O6A antigens is administered at an effective amount that is independently 40% or 50% of the first effective amount of the *E. coli* O25B antigen, each of the *E. coli* O25B, O1A, O2 and O6A antigen polysaccharides are independently covalently bound to a detoxified exotoxin A of *Pseudomonas aeruginosa* (EPA) carrier protein, and the first effective amount is 5 to 18 µg per administration, wherein said subject is a human.

11. The method of claim 10, wherein 8 µg of the O25B antigen polysaccharide is administered per administration.

12. The method of claim 10, wherein 16 µg of the O25B antigen polysaccharide is administered per administration.

13. The method of claim 10, wherein the *E. coli* O25B, O1A, O2 and O6A antigen polysaccharides are administered together in one composition.

14. The method of claim 10, wherein the *E. coli* O25B antigen polysaccharide comprises the structure of Formula O25B':

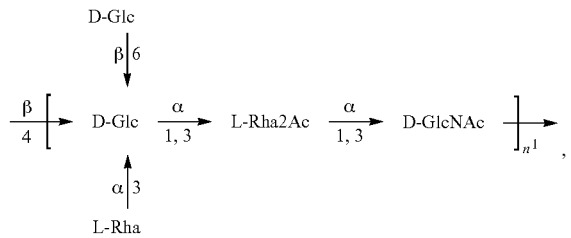

the *E. coli* O1A antigen polysaccharide comprises the structure of Formula O1A':

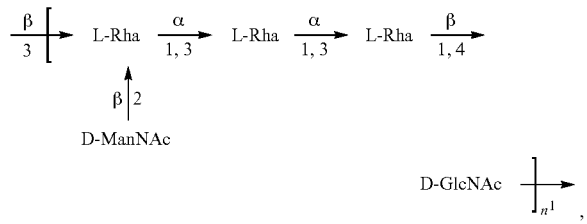

the *E. coli* O2 antigen polysaccharide comprises the structure of Formula O2':

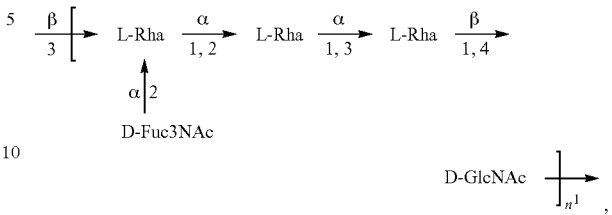

and
the *E. coli* O6A antigen polysaccharide comprises the structure of Formula O6A':

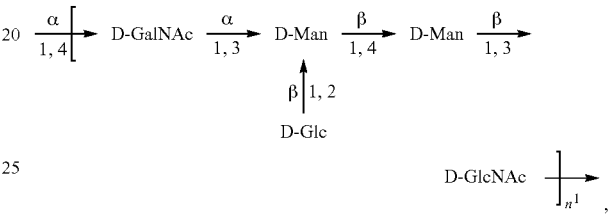

wherein n is independently an integer of 5 to 25, and
each of the *E. coli* O25B, O1A, O2 and O6A antigen polysaccharides are independently covalently bound to a carrier protein having the amino acid sequence of SEQ ID NO:1.

15. The method of claim 10, wherein the immune response limits the severity of or prevents an invasive ExPEC disease caused by ExPEC serotypes O1A, O2 and O6A and O25B in an at-risk human subject.

16. The method of claim 15, wherein the at-risk human subject has or is at risk of having an invasive ExPEC disease selected from the group consisting of urinary tract infection, a surgical-site infection, an abdominal or pelvic infection, pneumonia, nosocomial pneumonia, osteomyelitis, cellulitis, sepsis, bacteremia, a wound infection, pyelonephritis, meningitis, neonatal meningitis, peritonitis, cholangitis, soft-tissue infections, pyomyositis and septic arthritis.

17. A process of making a composition of claim 1, comprising combining the *E. coli* O25B antigen polysaccharide, the *E. coli* O1A antigen polysaccharide, the *E. coli* O2 antigen polysaccharide and the *E. coli* O6A antigen polysaccharide to thereby obtain the composition.

18. The composition of claim 1, wherein the first concentration is 10 to 36 µg/ml.

19. The multivalent immune composition of claim 6, wherein the first dose is 16 µg.

20. The method of claim 10, wherein each of the *E. coli* O1A, O2 and O6A antigens is administered at an effective amount that is 50% of the first effective amount of the *E. coli* O25B antigen.

* * * * *